United States Patent
Houbertz-Krauss et al.

(10) Patent No.: US 9,539,763 B2
(45) Date of Patent: Jan. 10, 2017

(54) METHOD FOR GENERATING BIOCOMPATIBLE THREE-DIMENSIONAL OBJECTS OR SURFACES BY LASER IRRADIATION, SUCH OBJECTS, THE USE THEREOF AND STARTING MATERIALS FOR THE METHOD

(75) Inventors: Ruth Houbertz-Krauss, Wuerzburg (DE); Matthias Beyer, Wuerzburg (DE); Joern Probst, Kuernach (DE); Thomas Stichel, Wuerzburg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 390 days.

(21) Appl. No.: 13/577,731

(22) PCT Filed: Feb. 8, 2011

(86) PCT No.: PCT/EP2011/051843
§ 371 (c)(1),
(2), (4) Date: Sep. 28, 2012

(87) PCT Pub. No.: WO2011/098460
PCT Pub. Date: Aug. 18, 2011

(65) Prior Publication Data
US 2013/0012612 A1   Jan. 10, 2013

(30) Foreign Application Priority Data
Feb. 12, 2010  (EP) .................................. 10153550

(51) Int. Cl.
*B29C 67/00* (2006.01)
*C07H 9/04* (2006.01)

(52) U.S. Cl.
CPC ............. *B29C 67/0066* (2013.01); *C07H 9/04* (2013.01)

(58) Field of Classification Search
CPC ........... B29C 67/0066; C07H 9/04; C08F 2/48
(Continued)

(56) References Cited

U.S. PATENT DOCUMENTS

| 5,582,876 A | 12/1996 | Langer et al. |
| 6,984,483 B1 | 1/2006 | Roscher et al. |

(Continued)

FOREIGN PATENT DOCUMENTS

| DE | 10111422 | 9/2002 |
| DE | 102008057684 | 5/2010 |

(Continued)

OTHER PUBLICATIONS

Claeyssens et al., "Three-Dimensional Biodegradable Structrues Fabricated by Two-Photon Polymerization", Langmuir 2009, 25, 3219-3223.*

(Continued)

*Primary Examiner* — Michael Pepitone
*Assistant Examiner* — Jessica Roswell
(74) *Attorney, Agent, or Firm* — Duane Morris LLP

(57) ABSTRACT

The present invention pertains to a process for producing three-dimensional, self-supporting and/or substrate-supported formed pieces or structures on surfaces by means of site-selective solidification of a liquid to pasty, organic or organically modified material within a bath consisting of this material by means of two- or multiphoton polymerization, whereby the material has at least one compound that has both an organic radical polymerizable via two-photon or multiphoton polymerization and a biocompatible, biodegradable or bioresorbable group, and/or wherein the bath material additionally contains groups or radicals, which are available for an inorganic crosslinking or which are already inorganically crosslinked, providing that both an organic radical polymerizable via two-photon or multiphoton (Continued)

(58) Field of Classification Search
USPC ....... 522/89, 144, 172; 536/4.1; 526/238.23,
526/279; 528/272; 525/411; 556/420;
566/420

See application file for complete search history.

(56) References Cited

U.S. PATENT DOCUMENTS

| 7,815,835 B2 | 10/2010 | Stampfl et al. |
| 2011/0288252 A1 | 11/2011 | Ballweg et al. |

FOREIGN PATENT DOCUMENTS

| EP | 0499435 | 8/1992 |
| EP | 1907192 | 11/2008 |
| WO | WO93/08506 | 4/1993 |
| WO | WO9525003 | 9/1995 |
| WO | WO9640002 | 12/1996 |
| WO | WO0104186 | 1/2001 |
| WO | WO03037606 | 5/2003 |

OTHER PUBLICATIONS

Houbertz-Krauss et al., machine English translation of WO 03/037606 (May 2003).*

Anseth et al., Photopolymerizable Degradable Polyanhydrides with Osteocompatibility, Nature Biotechnology, 1999, 17, pp. 1156-1159.

Bird et al., Preparation and Derivatives of Poly-(6-Omethacryloyl-D-galactose) and Poly-(6-O-acryloyl-D-galactose), J. Chem. Soc., 1966, pp. 1913-1918.

Heller et al., Poly(ortho esters): Synthesis, Characterization, Properties and Uses, Advanced Drug Delivery Reviews, 2002, 54, pp. 1015-1039.

Houbertz et al., Inorganic-organic Hybrid Materials for Application in Optical Devices, Thin Solid Films, 2003 442, pp. 194-200.

Ikeda et al., Lipase-Catalyzed Acylation of Sugars Solubilized in Hydrophobic Solvents by Compiexation, Biotechnology and Bioengineering, 1993, 42, pp. 788-791.

Claeyssens et al., Three-dimensional Biodegradable Structures Fabricated by Two-Photon Polymerization, Langmuir, 2009, 25, pp. 321-3223, XP002590369.

Salagean et al., Copolymerization of 3-O-Acryloyl-1, 2:5, 6-di-O-Isopropylidene-alpha-D-Glucofuranose and Butyl Acrylate at Different Molar Ratios, Chem. Bull. Politehnica Univ. Timisoara (RO), 2008, 53, No. 1-2, pp. 69-72, XP002590370.

Morrison et al. Lehrbuch der Organischen Chemie, 1974, Verlag Chemie, Weinheim, pp. 732-734, 741-742.

Kawata et al., Finer Features for Functional Microdevices, Nature, 2011, 412, pp. 697-698.

Kim et al., Synthesis and Characterization of Dextran-based Hydrogel Prepared by Photocrosslinking, Carbohydrate Polymers 1999, 40, pp. 183-190.

Landers et al., Rapid Prototyping of Scaffolds Derived from Thermoreversible Hydrogels and Tailored for Applications in Tissue Engineering, Biomaterials, 2002, 23, pp. 4437-4447.

Lang et al. Synthesis and Structural Analysis of Functionalized Poly (E-caprolactone)-Based Three-Arm Star Polymers, J. Polym. Sci. A: Polym. Chem., 2002, 40, 1127-1141.

Loy, Hybrid Organic-Inorganic Materials, MRS Bulletin, 2001, 26, 5, pp. 364-367.

Ohno et al., Nitroxide-controlled Free Radical Polymerization of Sugar Carrying Acryloyl Monomer, Macromol. Chem. Phys. 1999, 200, pp. 1619-1625.

Ouchi et al., Synthesis of Acryloyl-Type Polymer Fixing 5-Fluorouracil Residues through D-Glucofuranoses and its Antitumor Activity, J. Polym. Sci.: Part A: Polym. Chem. 1986, 23, pp. 2059-2074.

Zhang et al., Synthetic Nano-Fibrillar Extracellular Metrics with Predesigned Macroporous Architectures, J. Biomed. Mater. Res. 2000, 52, pp. 430-438.

Stampfl et al., Biodegradable Stereolithography Resins with Defined Mechanical Properties, Virtual, Rapid Manufac. Proc. VRAP, 2007, pp. 283-288.

Sun et al., Three-dimensionai Photonic Chrystal Structures Achieved with Two-Photon-Absorption Photopolymerization of Resin, Appl. Phys. Lett. 1999, 74, 786-788.

Sun et al., Real Three-dimensional Microstructures Fabricated by Photopolymerization of Resins through Two-Photon Absorption, Opt. Lett., 2000, 25, pp. 1110-1112.

Tian et al., Biodegradable and Biocompatible Inorganic-Organic Hybrid Materials, I. Synthesis and Characterization, J. Polym. Sci. A: Polym. Chem.1997, 35, pp. 2295-2309.

Tjia et al., Analysis of 3-D Microstructure of Porous Poly (lactideglycolide) Matrices Using Confocal Microscopy, J. Biomed. Mater. Res., 1998, 43, pp. 291-299.

West et al., Polymeric Biomaterials with Degradation Sites for Protease Involved in Cell Migration, Macromolecules, 1999, 32, pp. 241-244.

Wintermantel et al., Biodegradable Polymere, Medizintechnik Life Science Enginnering, 4th Ed. Springer, Berlin, 2008, pp. 143-268.

Zhang et al., Synthesis and Characterization of Biodegradable Hydrophobic-Hydrophilic Hydrogel Networks with a Controlled Swelling Property, J. Polym. Chem. 2000, 38, pp. 2392-2404.

* cited by examiner

METHOD FOR GENERATING BIOCOMPATIBLE THREE-DIMENSIONAL OBJECTS OR SURFACES BY LASER IRRADIATION, SUCH OBJECTS, THE USE THEREOF AND STARTING MATERIALS FOR THE METHOD

The present invention pertains to the production of biocompatible bodies molded as desired with three-dimensional structures, which can be either self-supporting and/or held by a support, by means of solidifying a polymerizable liquid. These bodies are suitable for many different purposes in the medical field, but especially as implants that are degradable, partly degradable or remaining in the body, which may possibly have been colonized with suitable cells before the implantation, as well as substrates for growing cell tissue or cells, whose contents shall be obtained, intended for an implantation. Especially structures or bodies can be generated in orders of magnitude of several cm up to below the μm range. Said bodies can be generated as a whole with the process according to the present invention; however, the process may possibly also be used to provide the surface of already present bodies with a three-dimensional, molded layer, which has the desired properties.

The present invention additionally pertains to the bodies obtainable or obtained with the process as well as uses thereof. Finally, the present invention pertains to suitable starting materials as well as a process for producing such starting materials, which do not cause any or cause only tolerably, low toxic reactions on the part of the physiological environment.

To achieve the purposes of the present invention, the bodies according to the present invention shall be biocompatible. By this term, it shall be understood that depending on the field of application the bodies shall in a first case be biodegradable, i.e., they shall be at least partly decomposable under physiological conditions by enzymes or other components present in the human or animal body or by means of the chemical environment, in which they are located. By "decomposable," it shall be understood that the physiological environment brings about the splitting of chemical-inorganic, organic or inorganic-organic such as carbon metal-bonds, as a result of which the coherence of the body is weakened or pores are formed, until the body, in the extreme case, is dissolved into smaller components, which are transported away within the body and ultimately are excreted or are further metabolized. Besides the said enzymatic processes, reference is made, above all, to the occurrence of an unspecific hydrolysis. If the biocompatible body is entirely or partially metabolized without a lasting inflammatory reaction, it shall be considered to be bioresorbable. The biodegradability and possibly bioresorbability of the bodies is desired, e.g., if they shall be used as bone implants, whose volume shall be replaced over time with endogenous bones. Something similar applies to porous bodies, which were precolonized with cells in vitro and shall be replaced after the implantation with a permanent cell composite, e.g., a piece of skin.

However, a partial or complete biodegradability within a reasonably short period is not desirable in all implants. For example, cartilage tissue is reproduced very slowly or no longer completely at all, so that cartilage implants shall remain for a very long time, if not for always, at least in the form of a residual supporting structure in the body, e.g., in the ear.

Finally, the present invention also pertains to substrates for the attaching and growing of cells which are possibly, but not necessarily intended for use in the human or animal body; however, in any case these offer a supporting structure, which feigns the presence of a physiological environment. This technical field is frequently called "tissue engineering." Thus, some cell types need a specific base to be able to grow, for example, endothelial cells need a base, which should be as similar as possible to the natural, collagen-containing basal membrane. The present invention pertains to substrates for letting such cell composites grow, which may later be used either at suitable sites as implants or can be used for obtaining endocrinically or exocrinically produced substances (hormones, interleukins, inflammatory mediators, enzymes or the like). Biodegradability is not necessary if an implantation is not being considered; however, the bodies according to the present invention must have on their surface groups that are adapted to the natural base of the respective cell types to the extent that metabolites of the cells can be obtained with them. This property can be called biocompatibility.

Above all, stereolithographic processes, but also two- or multiphoton polymerization by means of selective laser radiation of specific volumes (Volume pixel=Voxel) within a transparent bath were used in the past to produce three-dimensional bodies from polymerizable liquids. Stereolithographic processes are described, for example, in both WO patents 93/08506 and 95/25003, which indicate a liquid that can be solidified by radiation exposure, which is solidified into a three-dimensional body by means of (stereo)lithography layer by layer. Since the development of structures/components/structural elements in the area of sensory analysis, microengineering, data and telecommunications, electronics, chip technology and medical engineering tends towards structures always becoming smaller with simultaneous increase in the integration density as well as their functionality, two- or multiphoton polymerization was recently increasingly used to improve the structural properties. An only small space within the liquid to be solidified can be controlled with this process and especially with relatively good accuracy, which is solidified by means of the energy fed in. Therefore, the production of the molding can take place within a corresponding liquid, no longer (only) on its surface as in the stereolithographic process. The two- or multiphoton polymerization is described, for example, in H.-B. Sun et al., *Opt. Lett.* 25, 1110 (2000) and H.-B. Sun et al., *Appl. Phys. Lett.* 74, 786 (1999). A refined process for producing formed pieces is disclosed in DE 101 11 422.2. With this [process], a direct polymerization of a photosensitive resin in a site-selective manner within the bath volume, i.e., also possibly far below the bath surface, is possible with high accuracy. According to this process, radiation is used from a spectral range that is usually not absorbed by the photosensitive liquid while causing the solidifying effect. Thus, with not too high radiation intensities, the liquid is essentially transparent for the radiation used. The bath to be solidified is radiated with radiation, whose wavelength $\lambda$ amounts to approx. $n \times \lambda_0$, wherein $\lambda_0$ designates the wavelength, at which the liquid material would absorb radiation and the absorption process would be accompanied by an optical excitation upon initiation of the material solidification process. n is a whole number greater than 1. In practice, n is usually 2. If an increase in intensity is now produced by means of intensity concentration of the radiation within the liquid bath, at which multiphoton absorption, especially n-photon absorption (mainly with n equal to 2, but also, e.g., 3) takes place, then in the range of this locally increased intensity, the energetic excitation of the material can take place for inducing the solidifying effect due to radiation with light of wavelength λ, whereby this radiation penetrates the liquid in the manner already mentioned outside of the said zone of increased radiation intensity without triggering the solidifying effect. The zone of increased intensity can be achieved with relatively simple means by the beam being focused, possibly after previous beam expansion and ultrashort-pulse laser (femtosecond pulse laser) with high pulse peak intensities being used, so that the intensity is high enough only in the direct vicinity of the focus to achieve two-photon absorption (n=2) or multiphoton absorption (n=3, . . . ) in the liquid material. For producing a molding in the bath, the focus can then be guided to the sites to be solidified in accordance with geometry description data of the molding within the bath volume. A similar process was presented by Kawata et al. in a memo in *Nature*, Vol. 412, p. 697. Reference may also be made to the raid-protoyping processes, which are described by M. Lang, R. P. Wong, C.-C. Chu in *J. Polym. Sci. A: Polym. Chem.* 2002, 40, 1127-1141 and by H. Gruber, H. Lichtenegger, R. Liszka, R. Inführ, in EP 1 907 192 B1, 2008.

In contrast to the stereolithographic process, in production by means of femtosecond laser radiation, a three-dimensional body to be produced is therefore produced on a surface or—especially—in the volume in only one work step. This leads to no adverse gradient effects occurring in the component, which may absolutely occur in the stereolithographic process due to the manner of the production of formed pieces. However, specific gradients can be generated due to variation of, e.g., the incident power density, which leads to the formation of dense or less dense networks.

Moreover, there are various structuring processes, such as the synthesis via leeching processes (J. S. Tjia, P. V. Moghe, *J. Biomed. Mater. Res.* 1998, 43, 291-299; R. Zhang, P. X. Ma, *J. Biomed. Mater. Res.* 2000, 52 430-438). However, these have various weaknesses: The achievable structure sizes or scaffolds are either too small or considerably too large/coarse, their porosity cannot be specifically set or they lead to mechanically unstable scaffolds, which sometimes also degrade too rapidly, or the material cost for producing scaffolds or the production time is very high (J. Stampfl, M. Schuster, S. Baudis, H. Lichtenegger, R. Liska, *Virtual Rapid Manufac. Proc.* VRAP 2007, 283-288).

The materials used for this process are often organic thermoplasts (e.g., polymethyl methacrylate), which partly soften or melt already at temperatures starting from 80° C. Improved, inorganic-organic hybrid materials are disclosed in WO 03/037606 A1.

Frameworks for the growing of cells, so-called scaffolds, are partly produced by rapid prototyping. In *Biomaterials* 23: 4436-4447 (2002), R. Landers et al. describe the production of such scaffolds starting from thermoreversible hydrogels consisting of agarose, gelatin and agar. In *Langmuir* 25: 3219-3223 (2009), F. Claeyssens et al. presented three-dimensional structures, produced from the biodegradable three-block copolymer poly(ε-caprolactone-cotrimethylene carbonate)-b-poly(ethylene glycol)-b-poly(ε-caprolactone-cotrimethylene carbonate) by means of two-photon polymerization. A matrix is suggested in WO 96/40002 for the regeneration of tissue, which can be produced by means of stereolithography, laser sintering, three-dimensional printing or the like. The widest variety of materials are suggested for producing the matrix, including synthetic thermoplastic polymers, polyorthoesters, polymers of lactic acid and glycolic acid and other α-hydroxy acids as well as proteins such as albumin or collagen or polysaccharides.

Various classes of substances are suitable as biodegradable substrates. It is required that the material enters into a decomposition reaction under physiological conditions and does not cause any serious autoimmune reactions. Besides natural polymers known up to now, such as collagen or alginate, the polyesters, such as, among others, polyglycolic acid (PGA), polylactic acid (PLA) and polylactide-co-glycolic acid (PLGA), as well as polycaprolactone (PCL) are commercially available and have been approved by the FDA. Some of them are already commercially used as implant material (e.g., as bone pegs). The drawback of these polyesters is, however, that their degradation products lead to a sharp local reduction of the pH and thus cause inflammatory reactions, see E. Wintermantel et al., *Medizintechnik Life Science Engineering*, 4$^{th}$ edition, Springer, Berlin (2008), 143-268. S. H. Kim et al. describe a dextran-based hydrogel prepared by photocrosslinking in *Carbohydrate Polymers* 40 (1999) 183-190. For this, dextran was bromacetylated and then reacted with sodium acrylate, and the acrylated dextran was radiated with long-wave UV. Y. Zhang et al. presented a dextran-based, biodegradable, hydrophobic-hydrophilic hydrogel polymer with controlled swelling properties in *J. Polym. Chem.* 38 (2000) 2392-2404. They obtained it by the radiation of a mixture of acryloylated lactic acid and an allylisocyanate-modified dextran derivative.

Other materials derived from classes of natural substances may also be suitable for the production of substrates, when they are functionalized with crosslinkable groups. (Meth) acrylate groups were already frequently suggested for this in the past. In *Macromol. Chem. Phys.* 200 (1999), 1619-1625, K. Ohno et al. presented the sugar-containing acrylate, 2-O-acryloyl-1,2:5,6-di-O-isopropylidene-α-D-glucofuranoside, which could be polymerized by means of radical polymerization alone or in the form of a block copolymer. The acidolysis of these products yielded water-soluble or amphiphilic products. According to *Journal of Polymer Science: Part A: Polymer Chemistry* 23 (1986), 2059-2074, T. Ouchi et al. synthesized an acryloyl-like polymer, which can bind 1-β-carbonylethyl-5-fluorouracil radicals by means of ester bonds to D-glucofuranose for a completely different purpose, namely the controlled release of 5-fluorouracil in vivo. In both cases, the binding of the acrylates was brought about by means of acrylic acid chloride, a highly toxic compound. On the other hand, T. Bird et al. synthesized the 6-(meth)acryloyl ester of 1,2:3,4-di-O-isopropylidene-α-D-galactopyranose via esterification with methacrylic acid anhydride. The products could be unprotected and be thermally polymerized (in the presence of an initiator) into water-soluble products that can be oxidized into sugar acids. The Na salts of the sugar acids in turn proved to be viscous polyelectrolytes, see *J. Chem. Soc.* (C) 1966, 1913-1918.1. Ikeda et al. investigated the enzymatic acylation (with a lipase) of D-glucose with vinyl acrylate and subsequent polymerization in *Biotechnology and Bioengineering* 42 (1993) 788-791.

Besides sugars, polylactic acid derivatives were, above all, in the focus of researchers searching for biocompatible substrates. Extracellular matrices for tissue engineering shall be prepared according to the presentations of R. Zhang et al. in *J. Biomed. Mater. Res* 52 (2000) 430-438 using poly-L-lactic acid according to a complicated process, such that they reproduce the anatomical shape of the natural matrix, i.e., they have macroporous elements, fibers and interfiber spaces in the micrometer range. Such, also porous, matrices can be prepared from a poly(lactic acid-glycolic acid) copolymer according to the suggestions made by J. Tjia et al. in *J. Biomed. Mater. Res.* 43 (1998) 291-299. M. Lang et al., *J. Polym. Sci. A: Polym. Chem.* 40 (2002) 1127-1141, also describe the preparation of biodegradable poly-ε-caprolactone, which had been functionalized with maleic acid anhydride. The Michael system attached as a result of this might be used later for a radical polymerization of the caprolactone according to the presentations of the authors.

D. Tian et al. report in *J. Polym. Sci. A: Polym. Chem.* 35 (1997), 2295-2309 on materials that they obtained by reacting hydroxylated poly-ε-caprolactone with 3-isocyanatopropyl triethoxysilane or by reacting poly-ε-caprolactone modified with vinyl groups with triethoxysilane. Moreover, a hybrid material consisting of tetraethoxysilane and a sylated polycaprolactone was prepared.

The basic object of the present invention is to provide a process, by means of which desired, both large-dimensioned and extremely fine-structured, possibly porous, three-dimensional structures can be produced, which have the form of (possibly self-supporting) bodies or have the form of surface-structured or other layers. These bodies shall be biocompatible, biodegradable and/or bioresorbable and not have any toxicity to the body or bodies, with which they come into contact. Additionally, the present invention shall provide specific products with the properties mentioned as well as give use possibilities therefor. Finally, the present invention shall provide specific starting materials that are suitable for the process according to the present invention.

Moreover, the present invention pertains to the preparation of toxically safe acrylic acid derivatives and methacrylic acid derivatives of monomeric and oligomeric sugars as well as carbohydrates. Substances, which cause adverse side effects in the physiological environment, and especially a detectable, often strong immunological defense reaction, are called "toxic" within the framework of the present invention.

Said object is accomplished by a process for the production of three-dimensional, self-supporting and/or substrate-supported formed pieces or three-dimensional surface structures by means of the site-selective solidification of a liquid to pasty, organic or organically modified material within a bath consisting of this material by means of two- or multiphoton polymerization, whereby the material has one or more components, which are selected from among compounds with an organic radical polymerizable via two-photon or multiphoton polymerization and/or compounds which have at least one biocompatible, biodegradable or bioresorbable radical, providing that both an organic radical polymerizable via two-photon or multiphoton polymerization and a biocompatible, biodegradable or bioresorbable group must be contained in the material. "Three-dimensional surface structure" is defined as a layer applied according to the present invention to an already existing body having the desired shape. This means that this layer has a surface structuring either with essentially constant or with variable thickness and/or a contour following the shape of the already existing body.

The object is accomplished by providing the corresponding formed pieces with advantageous properties as well.

BRIEF DESCRIPTION OF THE DRAWINGS

Embodiments of the invention will now be described by way of example with reference to the accompanying drawings.

Figure 1:
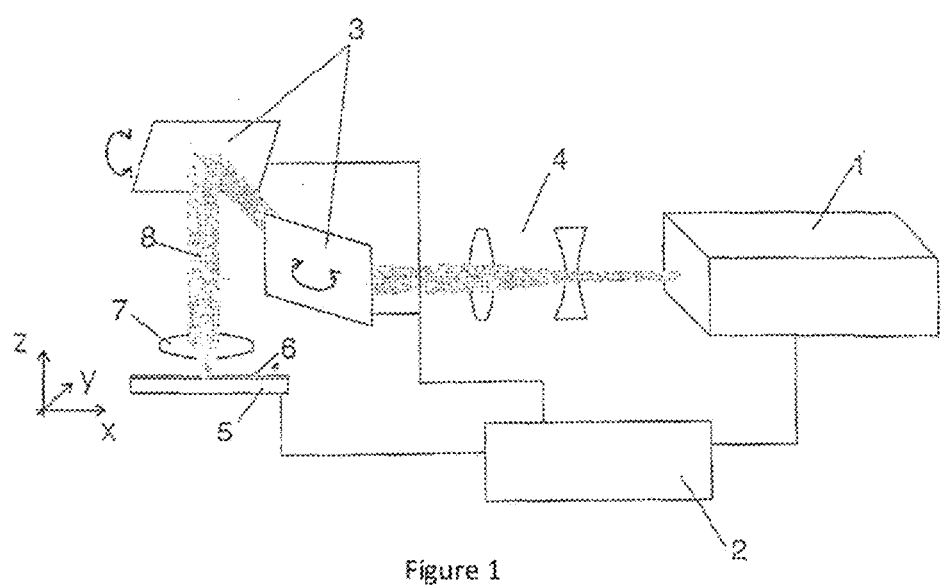
Fig. 1 shows, as an example, an arrangement for producing three-dimensional structures in accordance with the present invention.

In contrast to current processes for producing three-dimensional support structures, the technology of the present invention with regard to the material and the process is characterized in that (a) desired, three-dimensional support structures can be produced directly and rapidly in one material,
(b) a variable pore structure can be set from 100 nm up to in the mm range,
(c) a selective interconnecting pore structure can be obtained,
(d) a large-area structuring up to on the cm scale can be carried out with high precision and very high repeatability,
(e) sintering processes, as they must be applied in other processes (cf. state of the art), can be dispensed with,
(f) any number of extremely accurate copies of the structures can be produced,
(g) the structures are freely scalable, (h) patient-individual implants can be manufactured, whereby the geometric data from 3D scans (e.g., CT, laser triangulation) can be directly implemented in the manufacturing process,
(i) especially also visible light as well as infrared light by ultrashort pulses, i.e., by excitation by two- or multiphoton processes, can be used for the manufacture of structures,
(j) diode-pumped solid-state lasers or semiconductor lasers, fiber lasers, etc. can be used,
(k) biological components may also be integrated in the material precursor.

The present invention describes, among other things, production of at least partly physiologically degradable, biocompatible or bioresorbable substrates and functional elements, which may play a central role, e.g., in the regeneration of tissues and organs and the restoration of their function. The substrates or functional elements may be non-porous, e.g., in the form of nanostructures, or they may have a pore structure in the range between preferably 100 nm and 2 mm, which helps toward the better growing in of cells and their improved crosslinking. The structures may additionally or independently be used as drug delivery depots. Large-area, three-dimensional support structures having a suitable pore structure, which are necessary for, among other things, cell maturation, cell multiplication and cell differentiation, can especially be produced directly in three dimensions by means of multiphoton processes, wherein two- or three-photon processes are preferably applied. Processes of further higher order may also be proposed[.]

Among others, the materials mentioned in the introduction can be used as biodegradable substrates. Besides the polyesters mentioned there, however, still some other classes of substances are possible as biodegradable structural elements. In particular, these are:
1. Carbohydrates (mono-, di- and polysaccharides)
2. Amino acids, peptides and proteins, e.g., collagens or enzymes, as well as their lactam structures
3. Polyanhydrides
4. Polyorthoesters
5. Polyethers
6. Polycarbonates
7. Polyamides
8. Monohydroxy acids (especially α- or ω-hydroxy acids as well as their lactones and lactides) as well as their oligomers or polymers
9. The biocompatible, biodegradable or bioresorbable radical is therefore selected depending on need by the person skilled in the art. Favorable are radicals that have at least one (and preferably two or, more preferably, at least three) groups, which are each selected independently of each other from among —O—, —OC(O)O—, —C(O)NH—, —NHC(O)NH—, —NHC(O)O—, —C(O)OC(O)— or —C(O)O—, wherein these group(s) is/are especially preferably component(s) of a compound from the class of substances possible for this in each case as mentioned above, i.e., component(s) of a carbohydrate (mono-, di- or polysaccharides), an amino acid, a peptide or protein, e.g., a collagen or enzyme, or a lactam structure of the above-mentioned amino compounds, of a polyanhydride, of a polyorthoester, of a polyether, of a polycarbonate, of a polyamide or of a monohydroxy acid (especially of an α- or ω-hydroxy acid or of a lactone or lactide thereof) or of an oligomer or a polymer of the compounds cited in this paragraph, wherein these substances may be of natural or synthetic origin. In addition or as an alternative, the biocompatible, biodegradable or bioresorbable radical is selected from among radicals which can be split under physiological conditions in the human or animal body or by the involvement of microorganisms. Furthermore, favorable are aldose or ketose groups with a chain of at least 4 C atoms and at least 2 free or protected hydroxyl groups. The radicals preferably contain at least one di- or oligosaccharide, one di- or oligopeptide, one di- or oligoester, one di- or oligocarboxylic acid amide, one di- or oligoguanidine, one di- or oligoanhydride or one di- or oligourethane radical. They are especially preferably radicals with at least one carbohydrate, peptide, protein, polyanhydride, polycarbonate, polyorthoester, polyether, polyester, or polyamide group. Each of the above-mentioned radicals may have a single, several identical or a combination of several different of the above-mentioned groups. The material may contain identical or different radicals.

Within the framework of the present invention, the term "oligomer" is used for 2 to 5 consecutive, related structural units; a molecular structure with 6 or more such structural units is designated as a "polymer."

To obtain structurable biodegradable substrates, the above-mentioned physiologically degradable elements must be functionalized, so that a common crosslinking reaction, e.g., a polymerization or a polycondensation and thus a crosslinking initiated by external effects is made possible by means of photolithographic processes.

It is preferred for all embodiments of the present invention that two- or multiphoton polymerization of the organic radical polymerization via two-photon or multiphoton polymerization be carried out via one or more groups which can undergo radical polymerization. Also suitable are such systems according to the present invention which can be polymerized by means of a cationic UV starter, for example, epoxy systems (see, e.g., C. G. Roffey, *Photogeneration of Reactive Species for UV Curing*, John Wiley & Sons Ltd, (1997)). But, these systems tend toward parasitic polymerization, i.e., a polymerization also takes place in the non-exposed areas, which is why they may be not very suitable for areas of application with extreme requirements on the fineness and smoothness of the surfaces, e.g., high-resolution lithography (depending on modification). Suitable as groups capable of undergoing radical polymerization are nonaromatic C=C double bonds such as allyl groups or vinyl groups; however, they are especially preferably double bonds available for a Michael addition. Acrylate and methacrylate radicals are particularly preferred. The term (meth)acryl . . . is frequently used below to designate acrylic acid (derivatives) and/or methacrylic acid (derivatives) alone or combined. It should be pointed out that (meth)acrylate radicals in the sense of the present invention are not considered to be biocompatible, biodegradable or bioresorbable, even if they are linked via an ester group to the radical of the respective molecule.

In a first embodiment of the present invention, a purely organic material, which has the components according to the present invention, is used for the polymerization reaction: In this embodiment, the said material preferably contains at least one compound which has both an organic radical polymerizable via two-photon or multiphoton polymerization and a biocompatible, biodegradable or bioresorbable group.

According to this, the organic radical polymerizable via two-photon or multiphoton polymerization is preferably a radical capable of undergoing radical polymerization, which more preferably has at least one C=C double bond and particularly preferably a radical available for a Michael addition and especially a (meth)acrylate radical. This [radical] is connected in a suitable manner to the radical of the molecule. If it is a radical polymerizable via two-photon or multiphoton polymerization, e.g., a (meth)acrylate radical or a radical which has a free or activatable acid function, the linking may take place, for example, via an OH group during the formation of an ester function. This is especially favorable when the biocompatible, biodegradable or bioresorbable group is a sugar, a carbohydrate or a hydroxy acid or an oligomer/polymer of such an acid, because such a group usually has free hydroxyl groups. Another alternative is the linking via an isocyanate group, e.g., if the radical polymerizable via two-photon or multiphoton polymerization does not have an acyl function. The isocyanate group may react with a free hydroxyl group into a urethane group as a link between the two components.

Additional examples of materials that have both an organic radical polymerizable via two-photon- or multiphoton polymerization and a biocompatible, biodegradable or bioresorbable group, are polypeptides/polyamides, in which a terminal amino group or a free amino group is reacted within the molecule with an acid function, to which such an organic radical polymerizable via two-photon or multiphoton polymerization is additionally bound. These include, e.g., polypeptides/polyamides reacted with acrylic acid or methacrylic acid. These may be interrupted and/or additionally substituted in the chain by other groups such as polyethylene glycol or the like. As examples, $H_2C=CH-C(O)NH(As(As)_n)-PEG-(As(As)_n)-NH-C(O)-CH=CH_2$ may be mentioned, wherein $(As(As)_n)$ denotes an amino acid or a peptide with several, for example, 2-5 amino acids (for n=1-4). Such molecules with $(As(As)_n)$=Ala-Pro-Gly-Leu or Val-Arg-Asn are cited in J. West et al., *Macromolecules* (1999) 32, 241-244. Other examples are polyanhydrides, derived from saturated or unsaturated di- or polycarboxylic acids and an acid with a corresponding organic radical polymerizable via two-photon or multiphoton polymerization such as (meth)acrylic acid. $H_2C=CR-C(O)-(CH_2)_n-C(O)-CR=CH_2$ may be mentioned as an example. This compound is described with R=H and n=8 in K. S. Anseth et al., *Nature Biotechnology* (1999) 17, 1156-1159. Polycarbonates with acrylate or methacrylate groups are also known from the state of the art, e.g., compounds, which contain the group $-(C_6H_4)-X-(C_6H_4)-O-C(O)-O-$ as well as acrylate or methacrylate groups bound, wherein X may be =O, S, $SO_2$ or CO, see EP 499 435 A2. Polyorthoesters, which can be crosslinked via two-photon or multiphoton polymerization, are also known, e.g., (see J. Heller et al. *Advanced Drug Delivery Reviews* (2002), 54, 1015-1039). As examples of polyethers that are available for such a crosslinking reaction, reference may finally be made to the large number of polyethylene glycol di(meth)acrylates that are commercially available and are sold, for example, by Sigma Aldrich, including diacrylated and dimethacrylated PEG with molecular weights in the range of >200 up to approx. 6000, as well as dimethacrylated polypropylene glycol.

In this connection, the present invention discloses preferred functionalization reactions of classes of (potentially) physiologically degradable substances and materials, whose products are safer with regard to possible toxicity than those described in the state of the art. It is the linking of hydroxyl-group-containing starting materials, especially sugars, carbohydrates, sugar alcohols and saturated hydroxy acids as well as their oligo- and polymers, with acrylic acid and methacrylic acid groups. In the reactions usually used up to now, toxic by-products form, which are disadvantageous for the purpose of the present invention, since they can hardly be separated out and therefore remain in the objects produced in the process according to the present invention. Hence, according to the present invention, reactions with (meth)acrylic acid esters or with (meth)acrylic acid anhydride, whereby the latter is partly known from the state of the art, are used to produce the above starting materials. Accordingly, the present invention provides a process for preparing a compound with formula (A)

$$R'-CHR''-O-C(O)-CR'''=CH_2 \qquad (A)$$

wherein radical R''' is H or $CH_3$ and wherein R'CHR" is derived from a compound R'—CHR"OH, selected from among (a) Monosaccharides, namely aldo- and keto-pentoses, -hexoses and -heptoses with at least one (and preferably only one) free hydroxyl group, wherein the hydroxyl groups that are not free are present in the protected form, and especially as ethers or esters, e.g., boric acid ester, dimeric, oligomeric or polymeric carbohydrates, which contain at least one of the monosaccharides mentioned, (b) monomeric or oligomeric or polymeric sugar alcohols, obtainable by means of reduction of the aldehyde or keto group in the molecules mentioned under (a), (c) saturated monomeric, oligomeric or polymeric monohydroxy acids as well as their lactones and lactides, selected from among α-hydroxy acids with 3 or 4 carbon atoms and ω-hydroxy acids with 4-8 carbon atoms, characterized in that a compound

R'—CHR"OH

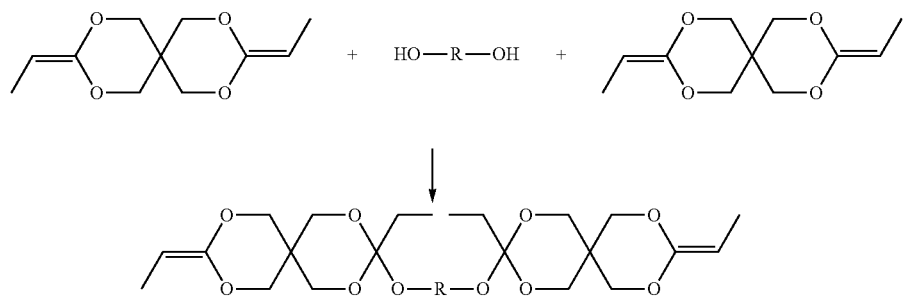

is reacted with a compound $$R^{IV}(O)-C(O)-CR'''=CH_2,$$

wherein $R^{IV}$ is an alkyl radical with preferably 1 to 20, more preferably with 1 to 10 carbon atoms, which may possibly be substituted with one or more $O—C(O)—CR'''=CH_2$ groups and preferably $CH_3$, $C_2H_5$ or $CH_2—CH_2—O—C(O)—CR'''=CH_2$, under conditions which shift the reaction equilibrium towards the product. Preferably, a large excess of (meth)acrylic acid, which may at the same time function as a solvent, is mentioned as a condition which shifts the reaction equilibrium towards the product. Instead of or in addition to this, a catalyst, e.g., an alkoxy titanate, may be used. Examples of suitable starting materials are C-6-pyranoses or furanoses or pure or mixed di- or polysaccharides derived therefrom, in which every two hydroxyl groups are twice protected by an isopropylidene group per sugar molecule, lactic acid, possibly derivatized polylactates and polymers of γ-butyro-, valerio- or caprolactone. Surprisingly, it turned out that when polylactones are used, depending on reaction control, the polymers are split with the (meth)acrylic ester during re-esterification, such that monomeric products of formula (A) are obtained from polymeric starting materials in some cases. Instead of the compound $R^{IV}O—C(O)—CR'''=CH_2$, acid bromide $Br—C(O)—CH_2—Br$ may also be used as a reaction partner, whereupon the product formed is reacted with sodium (meth)acrylate.

In the functionalization reactions via the anhydrides, re-esterification or by means of a nucleophilic substitution described above according to the present invention, especially toxic functionalization substances are avoided. The products are sugars, carbohydrates, polyethers or polyesters which may have a defined length and can be crosslinked by multiphoton processes and are thus structurable.

However, it is preferable to compose the substrates of the present invention of reactive monomers (or the preopolymers thereof), which besides an organically crosslinkable functionality as well as a biocompatible unit, additionally have an inorganic crosslinkability.

In a preferred embodiment of the present invention, for this reason, the bath material additionally contains groups or radicals that are available for inorganic crosslinking or are already inorganically crosslinked, including especially oligomerized or preferably polymerized units with —O—Si—O— or —O-M-O bonds with M equal to boron, aluminum or a transition metal. In particular, the bath material preferably contains an organopolysiloxane material that was obtained or is obtainable, for example, by means of hydrolysis and at least partial condensation of at least one silane of formula (I)

as well as possibly additionally at least one compound of the type

and/or of the type

and/or at least one not yet hydrolytically condensed compound (I) and possibly at least such a one of formulas (II) and/or (III), wherein $R^1$ is identical or different and represents an organic radical polymerizable via two- or multiphoton polymerization as defined above, $R^2$ is identical or different and is an organic radical not polymerizable in this manner, $R^3$ represents an alkoxy group (and with preferably 1 to 4 carbon atoms), and X is OH or a radical that is hydrolytically condensable under conditions of hydrolysis, subscript a is 0, 1, 2 or 3, subscript b is 0, 1 or 2 and a+b together are 0, 1, 2 or 3 and preferably 1, 2 or 3. Such inorganic-organic hybrid materials are known under the trademark ORMOCER® registered for the applicant and exist in a very wide variety. Bath materials consisting of silanes with a=1 which can be solidified by two-photon polymerization are described, for example, in WO 03/037606; such materials are also presented in R. Houbertz et al., *Thin Solid Films* 442 (2003), 194-200.

In this especially preferred embodiment of the present invention, the three components needed for the bath material, and particularly the organic radical polymerizable via two-photon or multiphoton polymerization, the biocompatible, biodegradable or bioresorbable radical and the group or radical, which is available for inorganic crosslinking or is already inorganically crosslinked, can be bound in any manner to one and the same structural unit in a first variant.

When the three above-mentioned components are bound to a single structural unit, then there are two possibilities: Either $R^2$ in the silane of formula (I) must be a biocompatible, biodegradable or bioresorbable radical or have such a radical, and a and b must each be at least 1, or the radical $R^1$ in this silane must, in addition to its property of being a radical polymerizable via two- or multiphoton polymerization, be biocompatible, biodegradable or bioresorbable or have a component with one of these properties. Then, $R^2$ may be selected at will or—in the case of b=0, be absent, see also claim 9.

Such silanes are, in principle, known from the state of the art. Thus, DE 10 2008 057 684.0 shows silanes that have an amino acid or a peptide as well as at least one (meth)acrylate group at a radical bound via carbon to the silicon atom. Such silanes can be obtained, for example, by reacting a trialkoxysilane, which, via, e.g., a propylene group, contains a methacrylate group and moreover a free (or activated) carboxylic group bound (or by reacting the corresponding polysiloxane obtained by means of hydrolytic condensation) with a free amino acid or a peptide with a free amino group, e.g., 3,4-dihydroxy-L-phenylalanine, under conditions that shift the reaction equilibrium towards the acid amide.

In a second variant, the three above-mentioned components may be bound to two structural units. In a first embodiment the organic radical polymerizable via two-photon or multiphoton polymerization and the biocompatible, biodegradable or bioresorbable radical may be component[s] of a purely organic compound, while the bath material additionally contains any organopolysiloxanes that were obtained or are obtainable by means of at least partial hydrolytic condensation from compounds of the type

as well as possibly additionally at least one compound of the type

and/or of the type

and/or not yet hydrolytically condensed compounds (I) and possibly (II) and/or (III), wherein the radicals and indices $R^1$, $R^2$, X, a, b and a+b are as defined above. However, it is especially preferred that a is at least 1. Then, the polycondensate can be incorporated into the organic network that forms during the polymerization of the purely organic compound by polymerization via the two-photon or multiphoton polymerization.

This embodiment is especially preferred. For example, these may be bath materials having acrylic-acid- or methacrylic-acid-functionalized mono-, di-, oligo- and/or polysaccharides and/or such a functionalized lactate or caproic acid derivative in combination with a monomeric or hydrolytically condensed compound (I) with a being equal to 1, wherein $R^1$ has preferably an acryl or methacryl group, e.g., ω-(meth)acryloxyalkyl trialkoxysilane. In such variants, the organic compound and the silane/polysiloxane can be organically polymerized together. Such bath materials may, of course, contain other additives, which are explained in detail below, for example (already condensed in or capable of being condensed in) silanes of formula (VI).

In a second embodiment, the bath material contains a purely organic compound having a radical polymerizable via two-photon or multiphoton polymerization as well as an organically modified polysiloxane, which is obtainable or was obtained by means of hydrolysis and by at least partial condensation of a starting material, which has at least one silane of formula (Ia")

$$R^1{}_aR^2{}_bSiX_{4-a-b} \tag{Ia"}$$

as well as possibly additionally at least one compound of the type $$M^{III}(OR^3)_3 \tag{II}$$

and/or of the type $$M^{IV}(OR^3)_4 \tag{III}$$

and, in addition to the polysiloxane or instead of this, at least one not yet hydrolytically condensed compound (Ia") as well as possibly compounds of type (II) and/or (III), wherein $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is OH or a radical hydrolytically condensable under conditions of hydrolysis, subscript a is 0, 1, 2 or 3, subscript b is 1 or 2 and a+b together are 1, 2 or 3. When a=0, products, which have an organic and an inorganic network independent of each other, which possibly interpenetrate, form during the radiation of this bath. For a=1, the siloxane component is additionally bound into the organic network via the polymerization of the radicals $R^1$.

In a third embodiment, the bath material contains (at least) one purely organic compound having a biocompatible, biodegradable or bioresorbable radical as well as an organopolysiloxane, which is obtainable or was obtained by means of at least partial hydrolytic condensation from compounds of the type $$R^1{}_aR^2{}_bSiX_{4-a-b} \tag{I}$$

as well as possibly additionally at least one compound of the type $$M^{III}(OR^3)_3 \tag{II}$$

and/or of the type $$M^{IV}(OR^3)_4 \tag{III}$$

and/or at least one not yet hydrolytically condensed compound (I) and possibly such a one of type (II) and/or (III), wherein the radicals and indices $R^1$, $R^2$, X and b are defined as above for formula (I), a is 1, 2 or 3 and a+b together are 1, 2 or 3.

As an alternative, there is also the possibility of using the three mentioned components in the form of a bath material, which contains silanes of formula (I) with a=1, 2 or 3 and silanes of formula (Ia) or a polycondensate consisting of at least these two silanes. Such materials are disclosed in DE 10 2008 057 684.0, e.g., a polysiloxane, which carries radicals $R^1$ as defined above on one part of the silicon atoms, e.g., methacrylate radicals (these can be obtained, as known from older state of the art, among other things, by linking a hydroxyl-group-containing methacrylate, such as glycerol-1,3-dimethacrylate to a silylisocyanate, for example, 3-isocyanato-propyl triethoxysilane) and carries radicals $R^2$ as defined above on another part of the silicon atoms, for example, an amino acid linked via an acid amide coupling group or such a peptide, obtainable by reacting an amino group of the amino acid or of the peptide with a silane, which contains an activated succinic acid group, for example, (triethoxysilyl)propyl succinic acid anhydride.

The physical and chemical properties of the bodies or layers generated using the above methods are excellent. The bodies, layers or their structures can be generated from the cm range up to into the sub-μm range.

The preparation of organically modified polysiloxanes or silicic acid condensates (often also called "silane resins") and their properties has been described in a plethora of publications. Reference may be made here, as a representative, e.g., to Hybrid Organic-Inorganic Materials, MRS Bulletin 26 (5), 364ff (2001). Quite generally, such substances are usually prepared by means of the so-called sol-gel process, by hydrolysis-sensitive, monomeric or pre-condensed silanes being subjected to a hydrolysis and condensation, possibly in the presence of other co-condensable substances, such as alkoxides of boron, germanium or titanium, as well as possibly of additional compounds, which can be used as modifiers or network modifiers, or of other additives, such as fillers.

Particularly preferably, a material consisting of one or more (possibly at least partly hydrolytically condensed) silanes of formula (I) are used for the bath material, wherein, at least in one silane of formula (I), $R^1$ is identical or different and represents an organic radical polymerizable via two- or multiphoton polymerization, which contains one or more groups which are able to undergo radical polymerization. The reasons as well as preferred embodiments thereof are already explained further above in the description of these radicals.

Radical $R^1$ in formula (I) preferably contains a nonaromatic C=C double bond, especially preferably a double bond available for a Michael addition. In all formulas of the present invention, $R^2$ may be an unsubstituted or substituted alkyl, aryl, alkylaryl or arylalkyl group, whereby the carbon chain of these radicals can be interrupted possibly by O, S, NH, CONH, COO, NHCOO or the like. $R^2$ may also contain groups which can enter into an addition reaction with C=C double bonds, for example, SH groups. The group X is usually hydrogen, halogen, alkoxy, acyloxy or $NR^3{}_2$ with $R^3$ being equal to hydrogen or a lower alkyl. Alkoxy groups are preferred as hydrolytically condensable groups and especially lower alkoxy groups such as $C_1$-$C_6$-alkoxy.

The solidifiable organopolysiloxane can be produced using at least one other silane of formula (IV)

$$SiX_4 \tag{IV}$$

wherein X is identical or different and has the same meaning as in formula (I). A compound that can be readily used for this is tetraethoxysilane. By adding such silanes to the mixture to be hydrolyzed and to be condensed, from which the polymerizable bath material finally forms, the SiO portion of the resin, i.e., the inorganic portion, is increased. The biodegradability of these materials does not have priority; however, they can be used, e.g., as scaffolds.

Inversely, the organic siloxane polycondensate to be polymerized according to the present invention can be produced using at least one silane with formula (V)

$$R^1_a SiR^2_{4-a} \quad (V)$$

wherein $R^1$ and $R^2$ have the meaning given above for formula (I). As a result of this, the degree of crosslinking of the polycondensate is reduced, the degradability increases.

The mixture, from which the silane condensate is produced, can additionally contain at least one silanol of formula (VI)

$$R^4_a Si(OH)_{4-a} \quad (VI)$$

wherein $R^4$ may be identical or different and has the meaning of $R^1$ as defined in formula (I) or $R^2$ as defined in formula (I) in each case or is a straight-chain, branched or cyclic alkyl with preferably 1 to 10 carbon atoms or an aryl with preferably 6 to 20 carbon atoms and wherein subscript a is 1, 2 or 3, and preferably 2. Particularly preferred are compounds (VI) with $R^4$ equal to phenyl and/or a=2. Silanols are condensed into the inorganic network without the formation of water. The hydrolysis may therefore take place in the presence of these compounds using catalytically effective quantities of water; otherwise, the system may remain free from water. In a preferred embodiment of the present invention, disilanols of formula (VI) are used as the starting material to be hydrolyzed and to be condensed in the mixing ratio of 1:1 (mol/mol) with silanes of formula (I), which preferably contain at least one $R^1$ group.

When $R^1$ in formula (I) carries a C=C double bond (or when a purely organic compound having a radical carrying such a double bond is present in the bath material) and $R^2$ is not present in this formula (I.e., b=0) or does not have any functional groups, in a specific embodiment, at least one silane of formula (VII)

$$R^5_a SiX_{4-a} \quad (VII)$$

wherein $R^5$ carries a group which can be radically added to a C=C double bond, can be added to the material to be hydrolyzed and to be condensed. Corresponding condensates are then available for a polymerization by means of addition reactions of the $R^5$ groups of the silanes of formula (VII) on double bonds of the radicals $R^1$ of the silanes of formula (I).

The mixture to be hydrolyzed and condensed for the purposes of the present invention may contain other substances, e.g., preferably lower alkoxides, especially $C_1$-$C_6$-alkoxides, of metals of the third main group, of germanium and of metals of the second, third, fourth, fifth, sixth, seventh and eighth subgroup. Some of these compounds are already mentioned above as metal compounds (II) and (III).

All in all, the organically modified silicic acid polycondensate, from which bodies can be solidified by two- or multiphoton polymerization according to the present invention, should preferably have at least 10 mol. % groups (as $R^1$ of formula (I) or in the purely organic compound) available for a two-photon polymerization, in relation to the molar quantity of silicon atoms plus possibly, if present, the metal atoms of the third main group, of germanium and of the second, third, fourth, fifth, sixth, seventh and eighth subgroup (which form the reference of 100 mol. %).

In a preferred embodiment of the present invention, the liquid of the bath is solidified by means of radiation with femtosecond laser pulses. As lasers suitable for this, Ti-sapphire lasers can preferably be used (either with the basic wavelength of 780 nm or, depending on the absorption behavior of the liquid to be hardened, with the second harmonic at 390 nm); other NIR lasers (e.g., with emitted wavelengths of 800 nm up to approx. 1,500 nm) are also suitable. However, different laser radiation is also possible, provided that the light source used can beam into the bath with an intensity that is sufficient or suitable for a multiphoton excitation. In particular, short-pulse lasers offer this property at moderate average outputs. The material to be cured must be transparent for the laser wavelength used. If material to be solidified, e.g., at 390 nm were available for single-photon polymerization, any wavelength of 400 nm or above can be used for two- or multiphoton polymerization; depending on the resin, 500-1,000 nm are, above all, suitable because of the transparency conditions. If greater wavelengths are being used, the polymerization may be initialized even by an n-photon absorption, whereby n is greater than 2. The threshold fluence, at which the polymerization process starts, can be lowered by selecting suitable components, e.g., co-initiators and/or amine components with an increased multiphoton absorption cross section in the resin. Consequently, the size of the process window, in which the polymerization takes place, is increased.

Especially when femtosecond lasers are used as a radiation source, bodies/layers are obtained with a drastically increased lithographic resolution with no adverse side effects of the structuring, such as, for example, edge rounding, inhibition or low lithographic resolution. The conventional, partial, expensive preparation of layers that is usually used for structuring can be dispensed with here. As a result of this, the production of genuine, geometrically accurate, three-dimensional structures and components for optical, (di)electric, magnetic, mechanical, biochemical and medical applications is considerably more precise, faster and more reliable. Moreover, the manner and duration of radiation offer the possibility of varying the degree of crosslinking in a targeted manner, such that different physical properties (e.g., degradability of variable fastness) can be achieved as needed with one and the same material. Unlike the three-dimensional structuring by means of stamping, with this process not only can three-dimensional structures be produced on substrates, but three-dimensional, self-supporting bodies can be produced completely from the volume.

The two-photon polymerization brings about a polymerization of the organic radicals available for this reaction; in addition, in rarer cases, still another hydrolytic condensation reaction of not yet hydrolyzed radicals X on the silicon atom can also be brought about herewith or this can even be completed, provided that the bath still contains such radicals.

For initiation of the crosslinking reaction, a suitable initiator can be added to the physiologically degradable materials according to the present invention. However, the crosslinking reactions may especially also be carried out without initiator, so that components with conditionally toxic potential can also be dispensed with entirely.

FIG. 1 shows, as an example, an arrangement for producing three-dimensional structures: A laser, e.g., a pulsed laser for producing ultrashort laser pulses (pulse duration 10 psec to 10 fsec) is used as a radiation source (1). To control the quality of the laser focus, beam-forming lenses (4) can be used (e.g., a beam expansion for a smallest possible focus diameter). Two computer-controlled, rotating mirrors (3) are used to deflect the laser beam in a defined manner in the x and y direction. The laser beam (8) is focused into the resin (5) to be polymerized by means of a focusing lens (7). This lens is a single lens or a system of lenses, e.g., microscope lenses. The resin to be polymerized is located under or on a transparent substrate (6). The resin may either be radiated through the substrate (6) (see diagram), which in this case should have a high optical surface finish, or it may be located on the top side of the substrate and be radiated directly (with no mapping). The substrate with the resin can be moved in a defined manner by means of computer-controlled positioning systems in the x, y and z directions. This, together with the screening mirrors, makes it possible to move the laser focus in three dimensions through the resin or to move the resin through the focus. As an alternative, the focusing lens (7) can be moved in the z direction to move the focus in the z direction through the resin. The components laser (1), scanner (3), as well as all positioning units are controlled and checked by a PC (2).

A special advantage of the process discovered within the framework of the present invention is that three-dimensional bodies with an enormous transition steepness, a high aspect ratio and a very high resolution can be produced, so that any three-dimensional structures, be it in the form of (possibly self-supporting) bodies, be it in the form of surface-structured or other layers, which are possibly held by a substrate, can be generated. This means that undercuts or cavities can also be produced.

The limitation of the lithographic resolution when using optical lithography is not determined by the material itself (except for those systems that may possibly be subject to a parasitic polymerization, see above), but rather by the methods usually used for the structuring, e.g., exposure through a mask under proximity conditions; contact exposure would only be possible regardless of contamination of the masks used because of the very good adherence of organopolysiloxanes to almost all materials or by using expensive masks with special coating for this purpose. In addition, in the UV structuring of special organopolysiloxanes, there is the disadvantage of all radically polymerizable systems that in the presence of oxygen and depending on the photoinitiator used, an inhibition layer forms near the surface, which hinders the UV crosslinking of the material in these areas. This is more or less highly pronounced depending on the heteropolysiloxane used, but could not easily be avoided up to now without special precautions. As an alternative, with exclusion of oxygen, the exposure can be carried out under exposure to nitrogen, which leads, on the one hand, to success regarding the inhibition layer, but, on the other hand, offers no changes to the resolution limitation (proximity) and the equipment is also considerably more expensive. Therefore, another advantage of the structuring according to the present invention using organopolysiloxanes is that the body and/or surface components can be structured from the volume, i.e., completely with exclusion of atmospheric oxygen or only still in the presence of the oxygen dissolved in the resin/lacquer and dispensing with a nitrogen flushing.

As mentioned, resins are organopolysiloxane-based materials that can be selected in a large number and variety with regard to various physical, chemical and biological properties, since they can carry a large number of different functional groups, which influence the physical and chemical properties of the resin (e.g., network formers, network modifiers). These resins are especially advantageous for an application in the designated fields, therefore. Above all, the preferred use of femtosecond laser radiation of silane resins for structuring and producing three-dimensional structures according to the present invention, be it in the form of (possibly self-supporting) bodies, be it in the form of surface-structured or other layers, which are possibly held by a substrate, for biochemical and medical applications makes it possible to use the structural properties of the materials with high resolution. The basis of the polymerization process according to the present invention is, as mentioned, two-photon polymerization, whereby the inventors were able to make the determination that the cross section of interaction (the probability of two-photon absorption) of the organopolysiloxanes that can be used according to the present invention is sufficiently large to use this process for production of three-dimensional structures, be it in the form of (possibly self-supporting) bodies, be it in the form of surface-structured or other layers, which are possibly held by a substrate. In addition, the organic polymerization of organopolysiloxanes with two-photon polymerization preferred according to the present invention should offer the possibility of being able to carry out an initialization of the polymerization process without UV initiator, which should essentially depend on the power density beamed in (→temperatures necessary for this in the range of up to 200° C., which is far below the typical temperature stability of up to 270° C.).

In the materials described in the present invention, it is possible to produce in situ three-dimensional formed pieces with a constant, porous network within the molding over a large area by means of light-induced crosslinking processes, especially by means of multiphoton absorption technology over a wide wavelength range using the widest variety of laser and optical systems. Large structures and formed pieces with a size up to in the cm range can be produced with the process described.

The present invention is also suitable for a process for producing bodies for in-vitro multiplication of cells, whereby the bodies have the form of a three-dimensional support matrix, which is used as a cell-supporting substance and/or lead structure for the extracellular matrix formed by the cells or offers cells the possibility of finding a three-dimensional arrangement that makes it possible for the cells to multiply and/or reach their genetically determined differentiation. Subsequently, the cells can be applied to the support matrix for multiplication and be cultivated; as an alternative, however, they may also be part of the liquid material precursor (of the bath material) already in the phase of the production process of the support matrix like other biological molecules (e.g. proteins such as collagen, enzymes, peptides, amino acids, antibodies, growth factors). The present invention also pertains to such bodies with applied cells.

For example, undifferentiated multipotent stem cells or genetically altered or native, differentiated cells of various types and degrees of differentiation may be used as cells.

The cells to be applied to the support matrix adhere to the matrix or multiply on this matrix mainly two-dimensionally, whereby together they can form an extracellular matrix or messenger substances (hormones). The support matrix is preferably porous, so that the inserted/applied cells penetrate it, assume a three-dimensional distribution and are able to trigger a three-dimensional tissue and organ growth or release messenger substances corresponding to their differentiation which was genetically determined or induced by means of added differentiation factors. The pore structures are selected as a function of the cell types that are to be applied to the support matrix; they usually have average diameters between 2 µm and 1 mm, preferably between 20 µm and 500 µm, and frequently between 40 µm and 250 µm. In an alternative embodiment of the present invention, the matrix is designed as a dense volume material that cannot be penetrated by the inserted/applied cells with the possibility of two-dimensional cell distribution and the simultaneous possibility of a three-dimensional tissue and organ growth in the sense of a "composite graft."

A preferred object of the present invention pertains to a cell composite, tissue and/or organs, which can be produced according to the process described above. Such a cell composite, such tissue and/or such organs is/are suitable, for example, as the in-vitro model for drug-tissue-organ interaction. For the production of tissues outside the human body, a wide variety of processes are used, which are summarized under the extensive term "tissue engineering." For this, depending on the type of tissue, cells are isolated from their existing tissue composite and multiplied. After this, the cells are either applied to flat materials of varying consistency or inserted into porous or gel-like materials, and as a result of this, the maturing of the tissue is induced and possibly stimulated by differentiation factors. The maturing of the tissue may take place outside or inside the body. The support matrix according to the present invention has the advantage that it is biodegradable and/or bioresorbable. E.g., the support matrix according to the present invention degrades and/or resorbs in such an embodiment preferably only after applying/inserting the cell composite, tissue and/or organ on/in an animal or human body.

Depending on the type of cell, the cells must either be dissolved beforehand by means of enzymatic digestion or by means of mechanical separation from their matrix composite or be excited to growth by applying or inserting onto/into a nutrient medium under physiological conditions. The support matrix mentioned above functions here as a lead structure for the cell growth or as lead structure for the accumulation of extracellular matrix and tissue components. According to the present invention, the substrate may be used in a variety of arrangements. The person skilled in the art knows which arrangement is to be selected on the basis of determining the (cell) tissue that is to be produced. The arrangements to be considered are as follows:

1. As a flat element, i.e., as a dense molding, which makes possible a penetration going beyond the dimension of the applied cells, but yet only limited (i.e., the average size of the holes is in no way larger, preferably even smaller than the average size of the cells to be cultivated; thus, the cells may grow in, but only in such a way that they adhere well to the substrate), with the essentially only, but at least primary possibility of two-dimensional cell distribution and extensive cell, tissue and organ growth. This can also be generated, e.g., by conventional UV lithography.

2. As a three-dimensional element, i.e., as a porous support matrix which can be penetrated by the cells (i.e., the average size of the holes is in no way smaller, but preferably even larger than the average size of the cells to be cultivated) with the possibility of three-dimensional cell distribution and a three-dimensional cell, tissue and organ growth. This can preferably be produced in situ using the multiproton absorption technology.

3. As a combination of 1) and 2) in the sense of a "composite graft" or organ by combining cells, tissues or organs and superficial involucrum (e.g., an organ capsule); this variant is considered for tissue structures which are composed of several types of cells. E.g., there are vessels consisting of endothelium and connective tissue, whereby the endothelium with flat structure is used to line a blood vessel, while the connective tissue functions as a support substance of the vessel and forms the three-dimensional hollow structure. Ultimately, a vessel can be reconstructed by combining 1) as flat element for the growth of endothelium and 2) as three-dimensional element for the growth of connective tissue.

Some tissue and cells types, which are especially suitable for multiplication/production by means of one of the three variants and therefore are preferred according to the present invention, are listed below.

For application 1) preferably the following tissues: Epithelium, endothelium, urothelium, mucosa, dura, connective tissue; and preferably the following cells: Multipotent stem cells, chondrocytes (cartilage; a two-dimensional medium is needed for chondrocyte multiplication; on the other hand, a three-dimensional medium is needed for chondrocyte differentiation and cartilage matrix formation. Here, with regard to cartilage, only the cells are intended when they dedifferentiate and multiply. The differentiation follows in application 2), osteocytes (bones; either two or three-dimensional, the same applies here as for the chondrocytes), nerve cells (nerves), hair cells (inner ear hearing organ) or their progenitor cells of any differentiation stage (e.g., multipotent stem cells).

For application 2) the following cells: The cells described for application 1) after their extensive multiplication, organ-specific cells (e.g., hepatocytes, nephrocytes, cardiomyocytes, pancreocytes), cells of the CNS with/without endocrine function, e.g., retina, neurocytes, pineal gland, dopaminergic cells, angiogenic cells (e.g., angiocytes), cells with endocrine or exocrine function (e.g., islet cells, adrenal cells, salivary gland cells, parathyroid gland, thyrocytes), cells of the immune system (e.g., macrophages, B cells, T cells or their progenitor cells of any differentiation stage such as multipotent stem cells). Cells of the immune system are grown three-dimensionally, because they encounter a three-dimensional scaffold depending on the type of tissue) in the tissue after penetration of the blood-tissue barrier and release their action there three-dimensionally.

For application 3) the following cells/tissue/organs: Among others, trachea, bronchi, vessels, lymph tissue, urethra, ureter, kidney, bladder, adrenal gland, liver, spleen, heart, vessels, thyroid gland, tonsils, salivary glands, brain, muscle (smooth, striated), intervertebral disks, meniscus, heart, lung, gallbladder, esophagus, intestine, eye, ear.

Another application possibility of the material to be used in the present invention is the colonization of the material with cells that have an endocrine or exocrine function and release active ingredients (e.g., hormones, interleukins, inflammatory mediators, enzymes), which release an action inside or outside the body. I.e., the material used according to the present invention can, with its colonization with cells with endocrine or exocrine function, be used inside, but also outside the body for the production of the above-mentioned active ingredients, which are then made available as drugs to the body via prior-art methods. An action released outside the body can be used to influence tissue or cells with the released substance.

Another use of the support matrix is one as a physiologically degradable and/or bioresorbable bio-implant as guidance for endogenous wound healing under or on the skin, mucosa or in the interior of the body within the framework of surgeries on organs and tissues. For this, the material is, if possible, inserted by a physician as a flat element or three-dimensional element directly or together with other substances into the wound or organs/tissue, for example, during a surgery. Moreover, the support matrix can additionally be mixed with other active ingredients of different substance groups with the possibility of a positive effect on the tissue and organ differentiation by releasing an active and passive action at the site of the application, but also by action release at a remotely lying action site. For this, the above-mentioned therapeutically active ingredients especially include, on the one hand, anti-infectious active ingredients, but also, on the other hand, active ingredients supporting and modulating the inflammatory reaction as well as tissue differentiation, for example, on the one hand, growth factors (IGF, TGF, FGF, etc.), on the other hand, glucocorticosteroids and interleukins, but also chemotherapeutic and immunosuppressive agents.

Another aspect of the present invention pertains to the use of the cells, organs and tissue according to the present invention, after they have been mixed with drugs and/or active ingredients, as an in vitro model for drug-tissue-organ interactions. Consequently, animal experiments can be minimized or even avoided entirely.

For all of the applications mentioned above, i.e., use as individualized, usually (but not absolutely necessary) bioresorbable support structures in vivo (as an implant) or in vitro (see above: keyword "tissue engineering"), an as physiological as possible cell colonization (by endogenous, human or animal cells or by corresponding cells added in vitro) is desirable. The cell adsorption at the support structure can be promoted in a targeted manner, since cells usually bind to surfaces via membrane proteins, so-called integrins and in turn prefer certain functional groups such as amino or carboxy groups as binding partners. Corresponding or other suitable functionalities on the surfaces of the bodies according to the present invention can be made available in different ways: In situ by means of a suitable selection of the organic components, for example, on the organically modified alkoxy silanes, or by biological components such as amino acid sequences or proteins, which are integrated into the production process of these bodies, i.e., into the bath material. Another possibility is the subsequent biological or biochemical functionalization or surface modification of the structured, cured matrix. The interactions between the matrix material according to the present invention and the biological components of the physiological environment can take place by means of chemisorption (chemical bonds, such as covalent, ionic, dipole-dipole interactions or even mixed forms of these types of binding), physisorption (by means of Van-der-Waals interactions) or mixed forms of both types of binding.

Active ingredients, such as growth factors, may also be integrated into the matrix, which promote the formation of tissue-like structures from adhered cells.

In addition, an additional aspect of the present invention is the use as a monolith. Massive implants in any three-dimensional form can be used as drug delivery systems, e.g., of liquid drugs and, for example, be used subcutaneously. It is important that the matrix enclosing the active ingredient is likewise not toxic and does not form any reaction products with the active ingredient.

The present invention shall be explained in detail below on the basis of exemplary embodiments.

GENERAL EXAMPLE

Preparation of a Bath Material Consisting of Hydrolytically Condensed Silanes and Acrylated and Methacrylated Organic Compounds An inorganic-organic hybrid polymer was prepared from methacryloxypropyl trimethoxysilane and diphenylsilanediol in a molar ratio of 1:1 as described in WO 01/04186 A1. As a catalyst for the hydrolytic condensation, $Ba(OH)_2$ or even $Ba(OH)_2 \cdot 8H_2O$ was used.

The acrylated and methacrylated target compounds prepared below in Examples 1 through 5 were mixed with this hybrid polymer in different molar ratios (3:1, 1:1, 1:2 and 1:3) and treated for up to 30 minutes in an ultrasound bath at 45 kHz. Then, 2 wt. % photoinitiator (Irgacure® 39, Irgacure® Oxe01, Irgacure® Oxe02 or the like) were added and this mixture was dissolved for another up to 30 minutes in the ultrasound bath at 45 kHz.

General Example

Structuring by Means of Multiphoton Polymerization

The hybrid polymer described above is already inorganically crosslinked. Said target compounds together with the hybrid polymer are further organically crosslinked by means of the structuring by means of TPA (multiphoton polymerization) explained in detail below, so that new hybrid polymers with inorganic and organic crosslinking components form.

The machine based on the principle of multiphoton polymerization makes it possible to convert three-dimensional CAD files without additional work steps (e.g., molding, etching steps, sintering) into the desired, real functional element. For this, a focused ultrashort pulse laser is used, which scans the bath material (which is also called "resin" below) brought to a viscous consistency, line by line and layer by layer, according to the given CAD file and thus initiates polymerization (solidification) defined three-dimensionally by the laser focus. Depending on the parameter settings and the size of the sample, the preparation thereof lasts a few minutes up to several hours. For very small structures writing velocities lower than 0.5 mm/sec and exposure powers lower than 1 mW combined with a 100× immersion oil lens with an NA (NA=numerical aperture) of 1.4 are used, as a result of which resolutions of about 100 nm can be achieved. Larger structures in the mm and cm range can be prepared with writing velocities of up to 40 mm/sec and exposure powers of up to 50 mW. In this case, lenses with average NAs (e.g., 0.45) and long working distances, which guarantee resolutions of a few μm, are used. The step of developing in a 50/50 solution of methyl isobutyl ketone (MIBK) and isopropyl alcohol following the exposure is used to remove the non-solidified resin and needs between 5 and 30 min. depending on the size and complexity of the structure. Finally, the sample is rinsed off with isopropyl alcohol and dried for approx. 10 to 30 min.

General Example

Degradation Study

A few material formulations were cured for 1 hr. in a Teflon form under radiation with UV light of wavelengths 254 nm and 366 nm. The thus formed rods (25×2×2 $mm^3$) were weighed, placed in 1.5 mL of PBS solution (phosphate-buffered physiological saline solution with a pH of approx. 7.4) and removed after 1 day, 3 days, 7 days, 14 days, 21 days and 35 days, respectively, and then every 28 days. The samples were rinsed off with ultrapure water, dried for 1 hr. at 110° C. and left to stand at room temperature for cooling off. Then, the rods were weighed again and the percent weight loss as a function of time was determined. The PBS solution was changed, on average, every 3 days in order to prevent a saturation of the solution. The pH was measured at the time of each removal and each solution change in order to thus obtain indications of released acids.

Example 1

Functionalization of 1,2:5,6-Di-O-Isopropylidene-α-D-Glucofuranose with Acrylic Acid Ethyl Ester and Two-Photon Polymerization Using the Product

1.1 Preparation of (0.2 mmol) of 6-O-acroyl-1,2:5,6-Di-O-isopropylidene-α-D-glucofuranose 0.60 g (4.83 mmol) of para-methoxyphenol, 2.93 g (11.3 mmol) of 1,2:5,6-Di-O-isopropylidene-α-D-glucofuranose, 18 mL (25.3 g, 282.74 mmol) of acrylic acid ethyl ester and 0.60 g (2.03 mmol) of tetra(isopropyloxy)titanium were charged into a 50-mL Schlenck flask with microdistiller under nitrogen atmosphere and the red reaction solution was heated to 112° C. After 40 min., a colorless acrylic acid ethyl ester-ethyl alcohol azeotrope was distilled off at 74-75° C. After 2 hr. the solution was briefly cooled off in air and 11 mL of petroleum ether (b.p. 30-50° C.) and 2.2 mL of water were added, whereby a yellow precipitate precipitated out overnight. The precipitate was centrifuged off for 10 min. at 4,000 rpm, washed twice with 10-20 mL of pentane each and centrifuged off again. The organic solutions were combined and removed by distillation until a pale yellow solid remained behind. This solid was dissolved again in approx. 30 mL of petroleum ether and washed three times with 27 mL of water each and then three times with 0.5 M of sodium hydroxide solution each. The solvent was removed by distillation again and the pale yellow to white solid was dried using an oil pump vacuum.

Yield: 1.01 g (3.21 mmol, 28.4%)

$^1$H-NMR (CDCl$_3$, 23° C., 400.1 MHz, [ppm]): δ=1.30 (s, 3H, CH$_3$), 1.41 (s, 3H, CH$_3$), 1.52 (s, 3H, CH$_3$), 4.05 (m, 2H, CH$_2$), 4.24 (m, 2H, CH—C4+C5), 4.53 (d, $^3J_{H,H}$=3.79 Hz, 1H, CH—C2), 5.33 (d, $^3J_{H,H}$=1.77 Hz, 1H, CH—C3), 5.90 (m, 2H, CH—C1, C=OCH=CH$_2$ cis), 6.13 (dd, $^3J_{H,H}$=10.48 Hz, $^3J_{H,H}$=17.31 Hz, 1H, C=OCH=CH$_2$), 6.45 (d, $^3J_{H,H}$=17.43 Hz, 1H, C=OCH=CH$_2$ trans).—$^{13}$C-NMR (CDCl$_3$, 23° C. 100.6 MHz, [ppm]): δ=25.20, 26.17, 26.69, 26.80 (CH$_3$), 67.09 (CH$_2$), 72.40 (CH—C5), 76.18 (CH—C3), 79.72 (CH—C4), 83.26 (CH—C2), 105.03 (CH—C1), 109.31 (C$_q$=C5+C6), 112.29 (C$_q$—C1+C2), 127.68 (C=OCH=CH$_2$), 131.98 (C=OCH=CH$_2$), 164.69 (C=OCH=CH$_2$).

FT-IR (ATR, 23° C., [cm$^{-1}$]): ṽ=1729 (s, v(C=O)), 1635 (m, v(C=C)), 1157 (s, v(C—O)), 1013 (ss, v(C—O—C)), 802 (s, δ(CH$_2$)).

μ-Raman (23° C., [cm$^{-1}$]): ṽ=2947 (s, v(C—H$_{2/3}$)), 1735 (m, v(C=O)), 1639 (m, v(C=C)), 1441 (m, v(C—H$_{2/3}$)), 802 (s, δ(CH$_2$)).

1.2 Preparation of a Bath Material Using the (0.2 Mmol) of 6-O-Acroyl-1,2:5,6-Di-O-β-Isopropylidene-α-D-Glucofuranose Prepared According to 1.1 and an Inorganic-Organic Hybrid Polymer 63.6 mg (0.2 mmol) of 6-O-acroyl-1,2:5,6-Di-O-isopropylidene-α-D-glucofuranose and 540 g (1.4 mmol) of an inorganic-organic hybrid polymer consisting of 3-methacryloxypropyl trimethoxysilane and diphenylsilanediol in a 1:1 stoichiometry, which had been hydrolytically condensed under catalysis of Ba(OH)$_2$, were charged into a 5-mL rolled rim glass, whereupon the mixture was treated for 5 hr. at 50° C. in an ultrasound bath at 45 kHz. A fine, whitish, cloudy dispersion formed. After adding 12 mg (0.03 mmol, 2 wt. %) of Irgacure 369, this dispersion was treated for 10 min. at 45 kHz in the ultrasound bath.

1.3 Preparation of a Molding

The suspension obtained was organically polymerized by means of two-photon absorption (TPA) and structured as indicated above in the "multiphoton polymerization" general example.

Example 2

Functionalization of 1,2:5,6-Di-O-Isopropylidene-α-D-Glucofuranose with Methacrylic Acid Anhydride and Preparation of Formed Pieces Using the Product

2.1 Preparation of (3-methacroyl)-1, 2:5.6-di-(O)-isopropylidene-α-D-glucofuranose 2.95 g (11.3 mmol) of 1,2:5,6-Di-O-isopropylidene-α-D-glucofuranose were dissolved in a 100-mL Schlenck flask with reflux condenser under nitrogen atmosphere in 15 mL of dry pyridine and 3 mL (3.13 g, 20.28 mmol) of methacrylic acid anhydride were added. The reaction solution was heated for 3.5 hr. at 65° C. and 16 mL of water were added. The reaction solution was heated for another hr. at 65° C. and then at 30° C. for 17 hr., whereby the clear, colorless solution became milky and cloudy. The reaction solution was extracted with 3 mL, 6 mL and 10 mL of petroleum ether. The combined organic solutions were washed three times with 15 mL of water each and three times with 14 mL 5% sodium hydrogen carbonate solution. The solvent was removed by distillation and a white solid was obtained. This solution was washed with a small amount of an ethyl alcohol-water solution (14:10) and dried in the oil pump vacuum.

Yield: 1.70 g (5.18 mmol, 45.7%)

$^1$H-NMR (CDCl$_3$, 23° C., 400.1 MHz, [ppm]): δ=1.29 (s, 6H, CH$_3$), 1.40 (s, 3H, CH$_3$), 1.52 (s, 3H, CH$_3$), 1.94 (t, $^3J_{H,H}$=1.52 Hz, 3H, C=OCCH$_3$=CH$_2$), 4.04 (m, 2H, CH$_2$), 4.25 (m, 2H, CH—C4+C5), 4.52 (d, $^3J_{H,H}$=3.52 Hz, 1H, CH—C2), 5.28 (d, $^3J_{H,H}$=2.28 Hz, 1H, CH—C3), 5.61 (t, $^3J_{H,H}$=1.52 Hz, 1H, C=OCCH$_3$=CH$_2$ cis), 5.88 (d, $^3J_{H,H}$=3.8 Hz, 1H, CH—C1), 6.11 (s, 1H, C=OCH=CH$_2$ trans).—$^{13}$C-NMR (CDCl$_3$, 23° C. 100.6 MHz, [ppm]): δ=18.23 (C=OCCH$_3$=CH$_2$), 25.18, 26.15, 26.69, 26.77 (CH$_3$), 67.20 (CH$_2$), 72.49 (CH—C5), 76.40 (CH—C3), 79.87 (CH—C4), 83.24 (CH—C2), 105.03 (CH—C1), 109.28 (C$_q$=C5+C6), 112.23 (C$_q$—C1+C2), 126.51 (C=OCCH$_3$=CH$_2$), 135.78 (C=OCCH$_3$=CH$_2$), 165.92 (C=OCH=CH$_2$).

FT-IR (ATR, 23° C., [cm$^{-1}$]): ṽ=1716 (s, v(C=O)), 1631 (w, v(C=C)), 1159 (s, v(C—O)), 1021 (ss, v(C—O—C)).

μ-Raman (23° C., [cm$^{-1}$]): ṽ=2947 (s, v(C—H$_{2/3}$)), 1735 (m, v(C=O)), 1639 (m, v(C=C)), 1441 (m, v(C—H$_{2/3}$)), 802 (s, δ(CH$_2$)).

2.2 Preparation of a Curable Resin Using (3-Methacroyl)-1,2:5,6-Di-O-Isopropylidene-α-D-Glucofuranose Analogously to Example 1.2, the (3-methacroyl)-1,2:5,6-di-O-isopropylidene-α-D-glucofuranose formed was mixed with a hybrid polymer consisting of 3-methacryloxypropyl trimethoxysilane and diphenylsilanediol and then treated, whereby the components were used in the molar ratio of 33% modified sugar and 67% hybrid polymer.

2.3 Polymerization of the Resin Under UV Radiation

Figure 2:
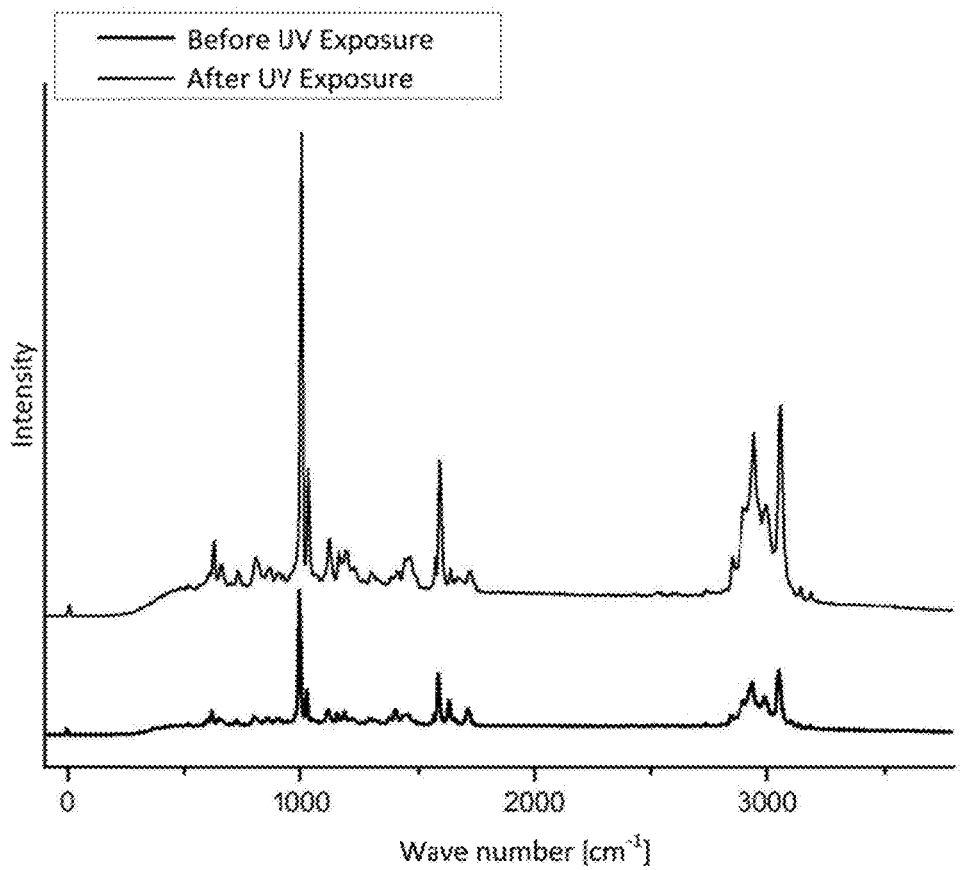
Fig. 2 depicts a μ-Raman spectrum of a particular resin polymerized using exposure to UV light, before and after polymerization.

The resin prepared according to 2.2 was filled in a form and organically polymerized (cured) using exposure to UV light. The μ-Raman spectrum before and after polymerization is shown in FIG. 2. A marked decrease of the C=C band is seen at 1639 cm$^{-1}$ compared to the C=O band at 1718 cm$^{-1}$ as a result of the organic crosslinking.

2.4 Preparation of a Molding by Means of Two-Photon Absorption

Figure 3:
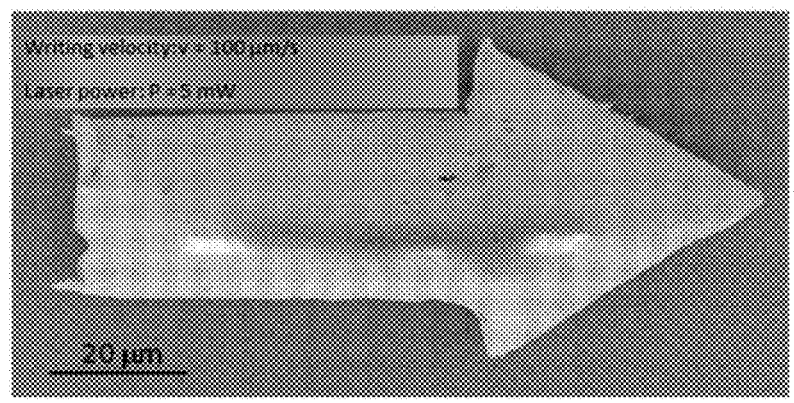
Fig. 3 shows a particular molding prepared by means of two-photon absorption.

The resin prepared according to 2.2 was organically polymerized by two-photon absorption (TPA) and structured as indicated above in the "multiproton polymerization" general example. A molding prepared in this way is shown in FIG. 3.

Example 3

Functionalization of Polycaprolactone-Diol with Acrylic Acid Ethyl Ester, Preparation of Formed Pieces Using the Product and Degradation Study Thereon

3.1 Preparation of (6-Acroyl)Hexanoic Acid Ethyl Ester 9.00 g (16.98 mmol) of polycaprolactone-diol, 26.5 mL (37.2 g, 372 mmol) of acrylic acid ethyl ester, 0.85 g (6.85 mmol) of para-methoxyphenol as well as 0.88 mL (0.84 g, 2.94 mmol) of tetra-(isopropyloxy)-titanium were charged under nitrogen atmosphere in a 100-mL Schlenck flask with microdistiller and the red reaction solution was heated at 113° C. After 40 min. a colorless acrylic acid ethyl ester-ethyl alcohol azeotrope was distilled off at 74-75° C. After 2 hr. the solution was cooled off in air for 30 min. and 16.1 mL of petroleum ether (b.p. 30-50° C.) and 3.2 mL of water were added, whereby after 4.5 hr. a yellow precipitate precipitated out. The precipitate was then centrifuged off after another 15 hr. for 10 min. at 4,000 rpm, washed twice with pentane and then centrifuged off again. The organic solutions were combined and washed three times with 40 mL of water each. The solvent was removed by distillation, so that a yellow solution remained behind. This solution underwent fractional distillation at 7×10$^{-3}$ mbar and 50-62° C., whereby a colorless liquid was obtained. This colorless liquid was then still purified by column chromatography (eluent:n-pentane:ethyl acetate=10:1).

Yield: 3.41 g (5.34 mmol, 31.4%)

$^1$H-NMR (CDCl$_3$, 23° C., 400.1 MHz, [ppm]): δ=1.19 (t, $^3J_{HH}$=7.32 Hz, 3H, OCH$_2$CH$_3$), 1.36 (m, 2H, OCH$_2$CH$_2$CH$_2$CH$_2$CH$_2$C=O), 1.62 (m, 4H, OCH$_2$CH$_2$CH$_2$CH$_2$CH$_2$C=O), 2.24 (t, $^3J_{HH}$=7.56 Hz, 2H, OCH$_2$CH$_2$CH$_2$CH$_2$CH$_2$C=O), 4.07 (m, 4H, OCH$_2$CH$_2$CH$_2$CH$_2$CH$_2$C=OOCH$_2$CH$_3$, 5.75 (dd, $^2J_{HH}$=1.52 Hz, $^3J_{HH}$=10.36 Hz, 1H, OC—OCH—CH$_2$ cis), 6.05 (dd, $^3J_{HH}$=10.36 Hz, $^3J_{HH}$=17.43 Hz, 1H, OC=OCH=CH$_2$), 6.33 (dd, $^2J_{HH}$=1.52 Hz, $^3J_{HH}$ 17.43 Hz, OC=OCH=CH$_2$ trans).—$^{13}$C-NMR (CDCl$_3$, 23° C. 100.6 MHz, [ppm]): δ=13.27 (OCH$_2$CH$_3$), 23.57, 24.51, 27.30, 33.15, 59.24, 63.32 (CH$_2$), 127.52 (OC=OCH=CH$_2$), 129.54 (OC=OCH=CH$_2$), 165.25, 172.51 (C=O). FT-IR (ATR, 23° C., [cm$^{-1}$]): ṽ=3100-3000 (w, v(=C—H)), 2945, 2866 (m, v(—C—H)), 1722 (s, v(—C=O)), 1636, 1620 (w, v(—C=C)), 1511, 1457, 1408 (m, δ(—CH$_2$)), 1374, 1270, 1186, 1098, 1061, 1035 (s, v(—C—O—C)).

μ-Raman (23° C., [cm$^{-1}$]): ṽ=1072, 1199, 1304 (v(—C—O—C)), 1412, 1453 (δ(CH$_2$)), 1639 (v(C=C)), 1726 (v(—C=O)), 2939 (v(—C—H)), 3042, 3072, 3109 (v(=C—H)).

3.2 Polymerization of (6-Acroyl)Hexanoic Acid Ethyl Ester

Figure 4:
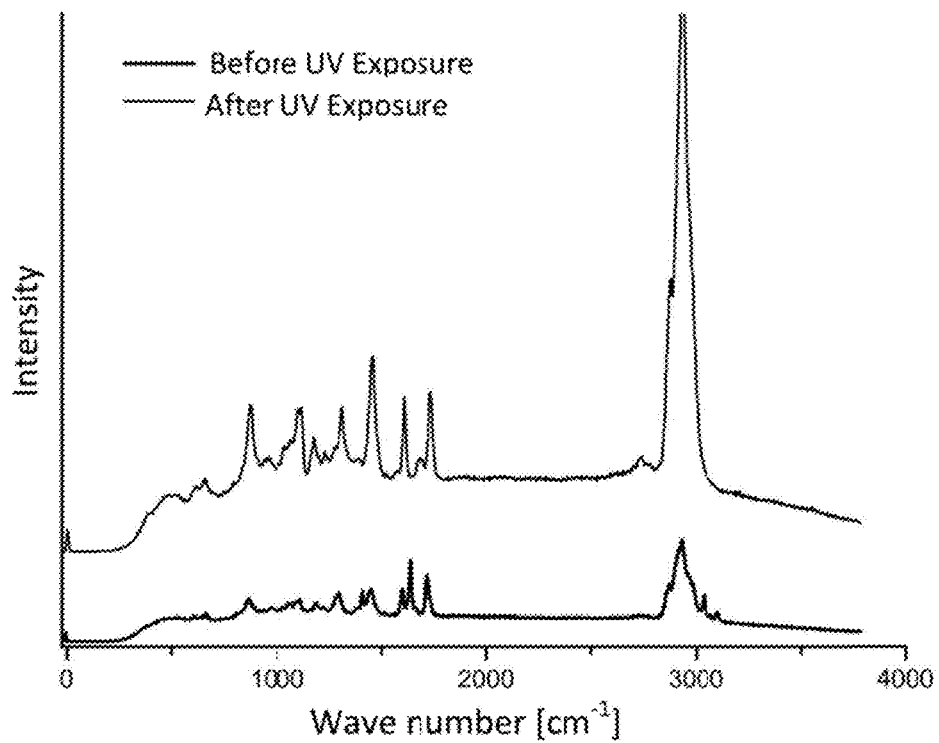
Fig. 4 depicts a μ-Raman spectrum of (6-acroyl)hexanoic acid ethyl ester polymerized using exposure to UV light, before and after polymerization.

The (6-acroyl)hexanoic acid ethyl ester that was prepared according to 3.1. was mixed with 2 wt. % Irgacure® 369 as the photostarter and crosslinked by exposure to UV light. The μ-Raman spectrum before and after polymerization is shown in FIG. 4. A marked decrease in the C=C band is seen at 1634 cm$^{-1}$ compared to the C=O band at 1738 cm$^{-1}$ as a result of the organic crosslinking.

Figure 5:
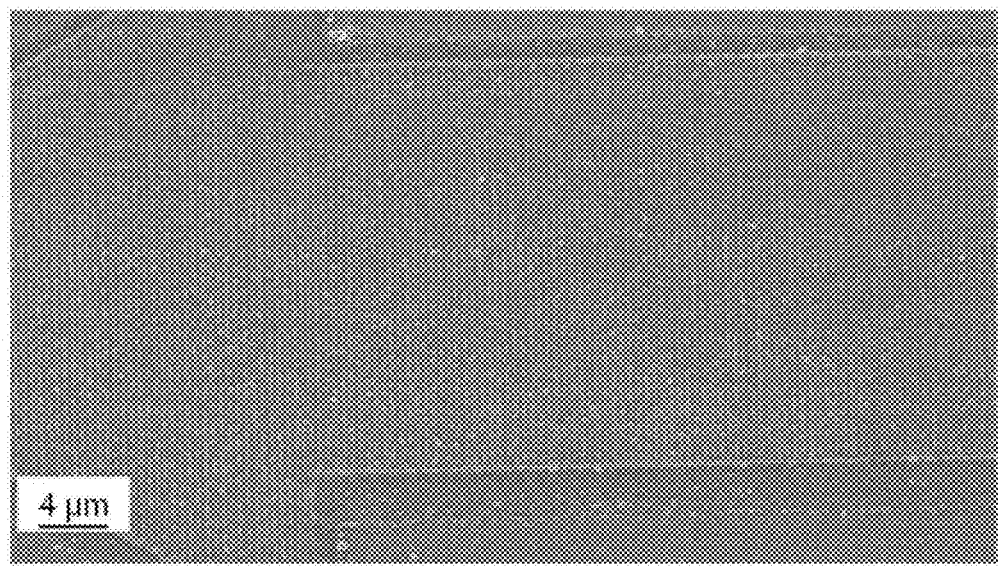
Fig. 5 shows a molding prepared from (6-acroyl)hexanoic acid ethyl ester by means of two-photon absorption.

3.3 Preparation of a Molding from (6-Acroyl)Hexanoic Acid Ethyl Ester by Means of Two-Photon Absorption The (6-acroyl)hexanoic acid ethyl ester that was prepared according to 3.1. was mixed with 2 wt. % Irgacure® 369 as the photostarter and organically polymerized by means of two-photon absorption (TPA) and structured as indicated above in the "multiphoton polymerization" general example. A molding prepared in this manner is shown in FIG. 5.

3.4 Preparation of a Curable Resin Using the (6-Acroyl)Hexanoic Acid Ethyl Ester Prepared According to 3.1 and an Inorganic-Organic Hybrid Polymer Analogously to Example 1.2, the (6-acroyl)hexanoic acid ethyl ester was mixed and treated with a hybrid polymer consisting of 3-methacryloxypropyl trimethoxysilane and diphenylsilanediol, whereby the components were used in the molar ratio of 50% (6-acroyl)hexanoic acid ethyl ester and 50% hybrid polymer.

Figure 6:
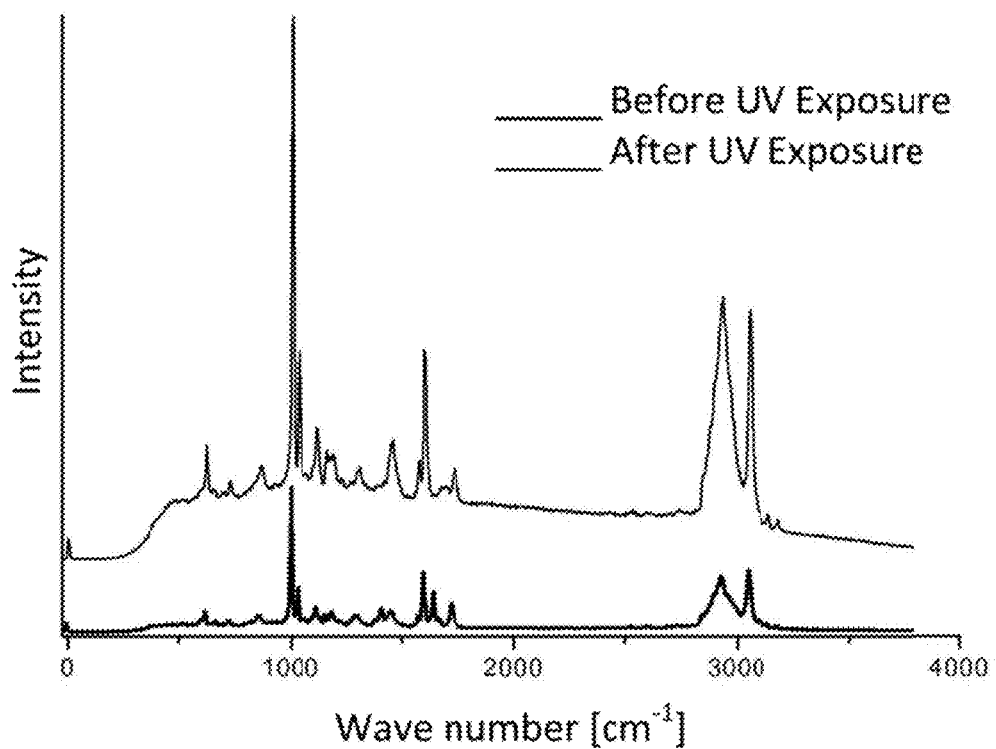
Fig. 6 depicts a μ-Raman spectrum of a particular resin polymerized using exposure to UV light, before and after polymerization.

3.5 Polymerization of the Resin Obtained According to 3.4. Under UV Radiation The resin prepared according to 3.4 was filled in a form and then organically polymerized (cured) by means of exposure to UV light. The μ-Raman spectrum before and after polymerization is shown in FIG. 6. A marked decrease in the C=C band is seen at 1639 cm$^{-1}$ compared to the C=O band at 1718 cm$^{-1}$ as a result of the organic crosslinking.

3.6 Preparation of a Molding by Means of Two-Photon Absorption

Figure 7:
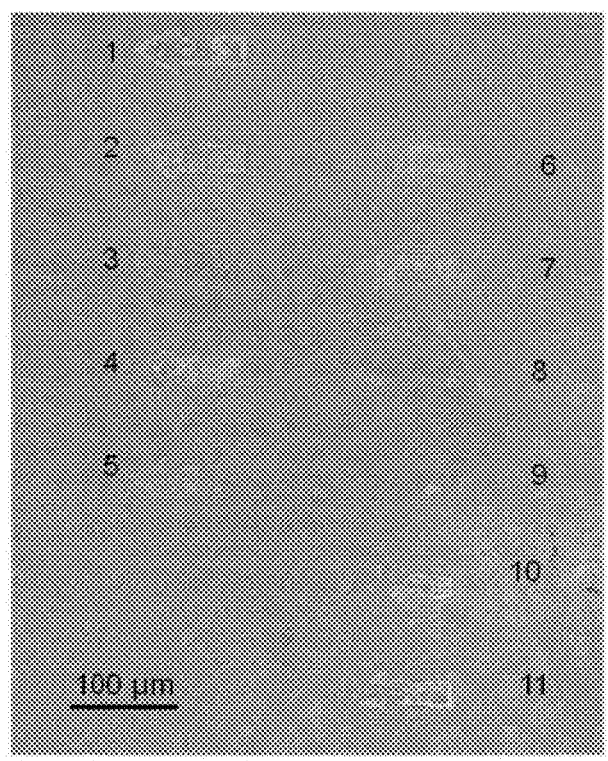
Fig. 7 shows particular formed resin pieces prepared by means of two-photon absorption.

The resin prepared according to 3.4 was organically polymerized by two-photon absorption (TPA) and structured as indicated above in the "multiphoton polymerization" general example. Formed pieces prepared in this manner (structured from a drop on a glass plate) are shown in FIG. 7.

3.7 Degradation Study

Figure 8:
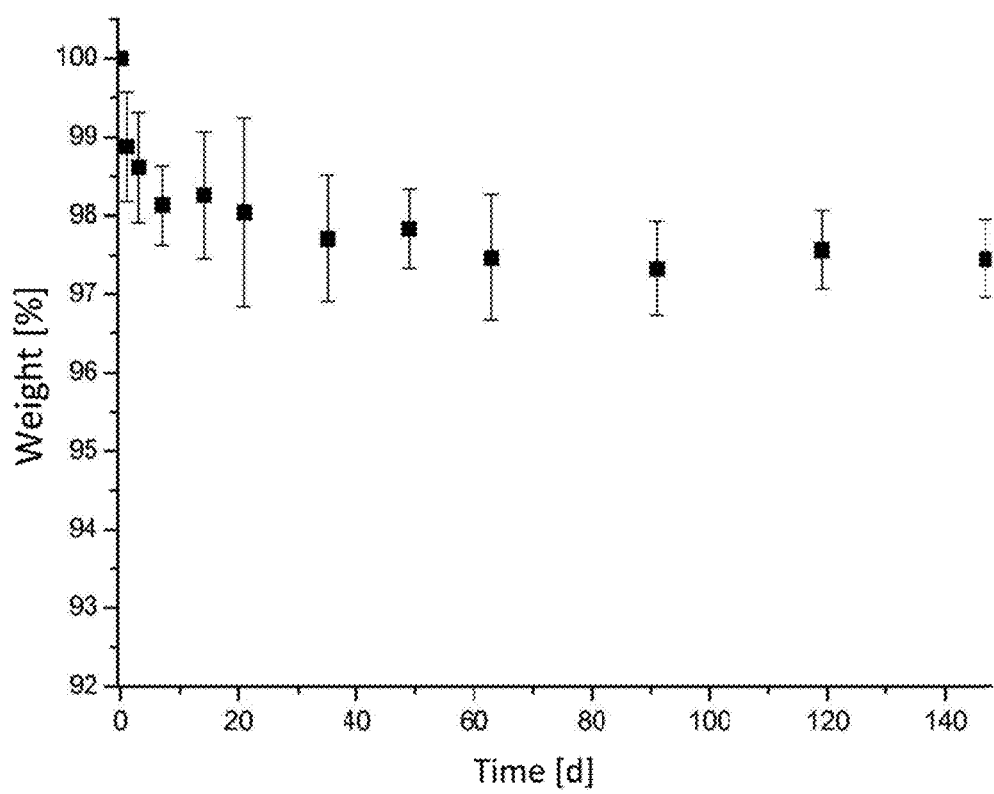
Fig. 8 graphically shows the result of a particular resin prepared in accordance with an embodiment of the present invention and placed in PBS solution.

The resin prepared according to 3.4 was cured as explained in the general example and then placed in PBS solution. The result is graphically shown in FIG. 8. In a comparison study with the inorganic-organic hybrid polymer without (6-acroyl)hexanoic acid ethyl ester, no degradation at all could be observed.

Example 4

Functionalization of Polycaprolactone-Diol with Methyl Methacrylate, Preparation of Formed Pieces Using the Product as Well as Degradation and Biocompatibility Studies Thereon

4.1 Preparation of (6-Methacroyl)Hexanoic Acid Methyl Ester 10.0 g (18.9 mmol) of polycaprolactonediol were dissolved under protective gas atmosphere in 29.7 mL (276 mmol) of methyl methacrylate and mixed with 991 mg (7.98 mmol) of p-methoxyphenol as well as 941 mg (3.31 mmol) of tetra(isopropyloxy)-titanium(IV), whereupon the solution turned dark red. While stirring it was heated at 110° C. and within 45 min. approx. 4 mL of an azeotrope of methyl alcohol and methyl methacrylate were distilled off (transition temperature ca. 45° C.). The mixture was allowed to cool off for 30 min. and 15.2 mL of n-pentane as well as 3.00 mL of water were added, as a result of which an orange precipitate precipitated out. This was removed by means of centrifuging and decanting and later washed twice with approx. 15 mL of n-pentane each. Filtrate and wash solutions were combined and then desolventized under reduced pressure. The light yellow residue was purified by distillation at $6.0 \times 10^{-3}$ mbar. Boiling point: 65° C., yield: 3.52 g (5.28 mmol, 28%) of a light purple liquid. NMR and UV Vis-spectrum showed that p-methoxyphenol impurities were still contained, which could be removed by column chromatography on a silica gel phase (eluent: 10:1 mixture of n-pentane and ethyl acetate).

Yield: 713 mg (3.33 mol, 8.8%)

$^1$H-NMR (CDCl$_3$, 23° C., 400.1 MHz, [ppm]): δ=1.35 (m, 2H, OCH$_2$CH$_2$CH$_2$CH$_2$CH$_2$C=O), 1.62 (m, 4H, OCH$_2$CH$_2$CH$_2$CH$_2$CH$_2$C=O), 1.87 (t, $^4J_{HH}$=1.26 Hz, 3H, OC=OCCH$_3$=CH$_2$), 2.26 (t, 2H, $^3J_{HH}$=7.45 Hz, OCH$_2$CH$_2$CH$_2$CH$_2$CH$_2$C=O), 3.60 (s, 3H, OCH$_3$), 4.08 (t, $^3J_{HH}$=6.57, 2H, OCH$_2$CH$_2$CH$_2$CH$_2$CH$_2$C=O), 5.48 (m, 1H, OC=OCCH$_3$=CH$_2$ cis), 6.02 (m, 1H, OC=OCCH$_3$=CH$_2$ trans).—$^{13}$C-NMR (CDCl$_3$, 23° C. 100.6 MHz, [ppm]): δ=18.46 (OC=OCCH$_3$=CH$_2$), 24.81, 25.72, 28.45, 38.06 (CH$_2$), 51.67 (OCH$_3$), 64.58 (CH$_2$), 125.41 (OC=OCCH$_3$=CH$_2$), 136.59 (OC=OCCH$_3$=CH$_2$), 167.62, 174.12 (C=O).

FT-IR (ATR, 23° C., [cm$^{-1}$]): ṽ=3100-3000 (w, v(=C—H)), 2951, 2863 (m, v(—C—H)), 1715 (s, v(—C=O)), 1636 (w, v(—C=C)), 1510, 1438 (m, δ(—CH$_2$)), 1321, 1296, 1234, 1162, 1101, 1036 (s, v(—C—O—C)).

μ-Raman (23° C., [cm$^{-1}$]): ṽ=1011, 1050, 1101, 1161, 1178, 1258, 1296 (v(—C—O—C)), 1403, 1448 (v(CH$_2$)), 1635 (v(C=C)), 1714 (v(—C=O)), 2925 (δ(—C—H)), 3062, 3105 (v(=C—H)).

4.2 Preparation of Curable Resins Using the (6-Methacroyl)Hexanoic Acid Methyl Ester Prepared According to 4.1

Analogously to Example 1.2, the (6-methacroyl)hexanoic acid methyl ester was mixed and treated with a hybrid polymer consisting of 3-methacryloxypropyl trimethoxysilane and diphenylsilanediol, whereby the components were used (a) in the molar ratio of 50% (6-methacroyl)hexanoic acid methyl ester and 50% hybrid polymer and (b) 25% (6-methacroyl)hexanoic acid methyl ester and 75% hybrid polymer.

Figure 9:
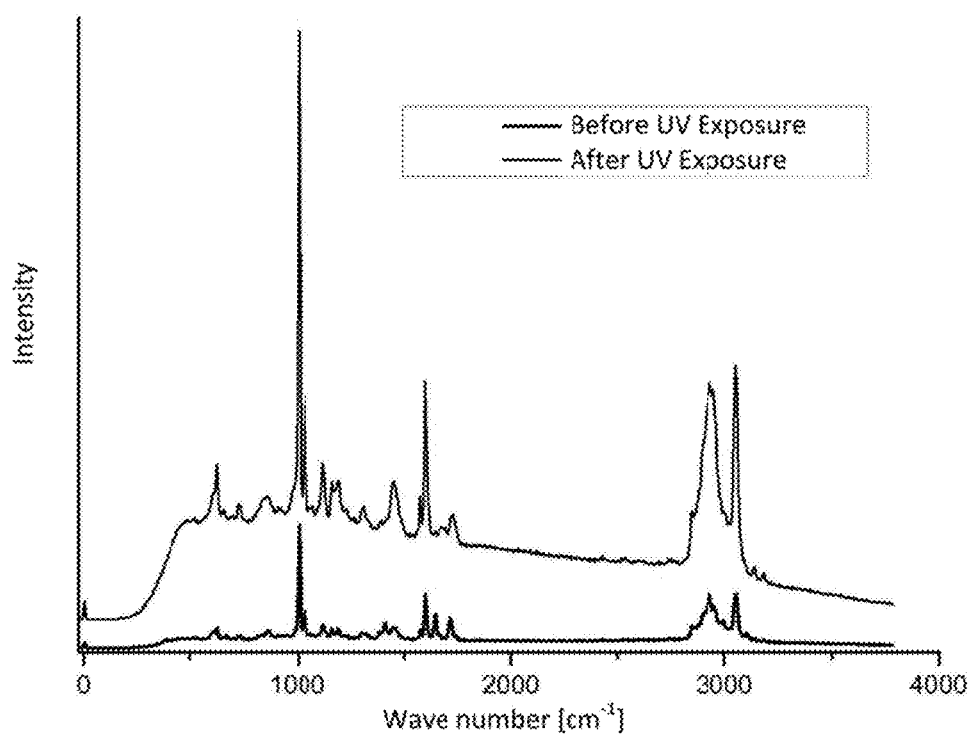
Fig. 9 depicts a μ-Raman spectrum of an alternative resin polymerized using exposure to UV light, before and after polymerization.

4.3 Polymerization of the Resin Obtained According to 4.2 Under UV Radiation The resin prepared according to 4.2, variant (a) was filled into a form and organically polymerized by means of exposure to UV light (cured). The μ-Raman spectrum before and after polymerization is shown in FIG. 9. A marked decrease in the C=C band is seen at 1646 cm$^{-1}$ compared to the C=O band at 1722 cm$^{-1}$ as a result of the organic crosslinking.

4.4 Preparation of a Molding by Means of Two-Photon Absorption

Figure 10:
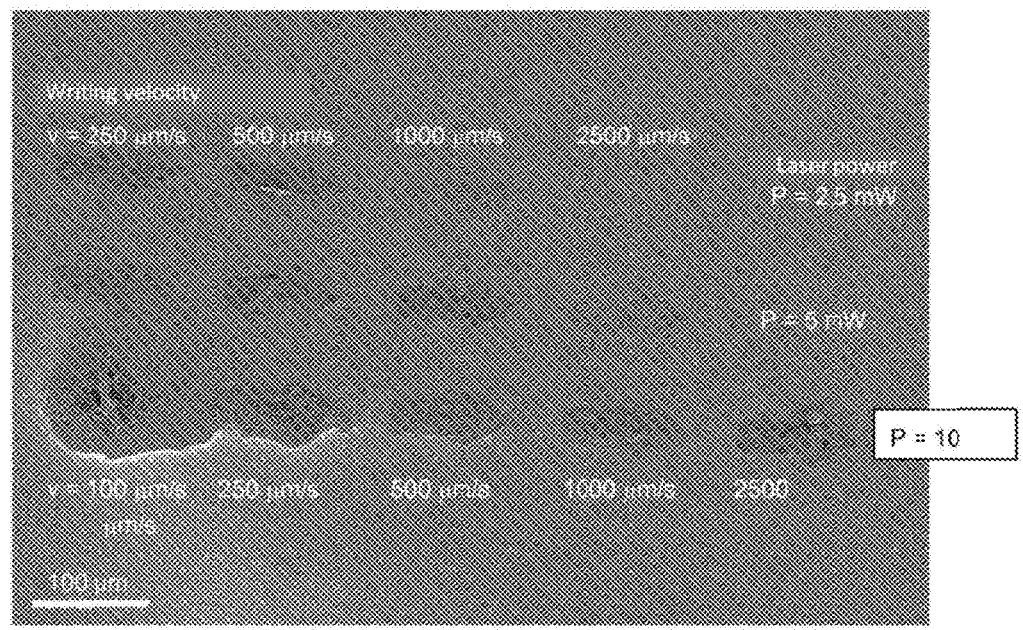
Fig. 10 shows particular formed resin pieces prepared by means of two-photon absorption.

The resin prepared according to 4.2, variant (a) was organically polymerized by means of two-photon absorption (TPA) and structured as indicated above in the "multiphoton polymerization" general example. Formed pieces prepared in this way are shown in FIG. 10.

4.5 Degradation Study

Figure 11:
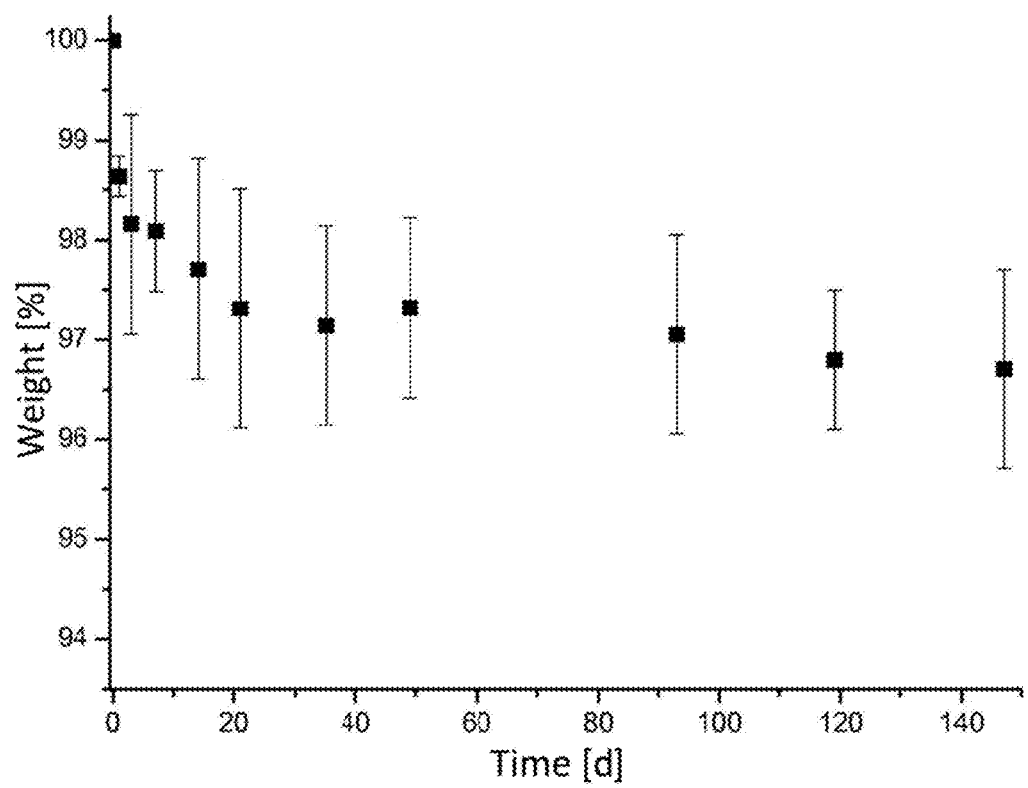
Fig. 11 graphically shows the result of a particular resin prepared in accordance with the present invention and placed in PBS solution.

The resin prepared according to 4.2, variant (a) was cured as explained in the general example and then placed in PBS solution. The result is graphically shown in FIG. 11.

4.6 Biocompatibility Study

Figure 12:
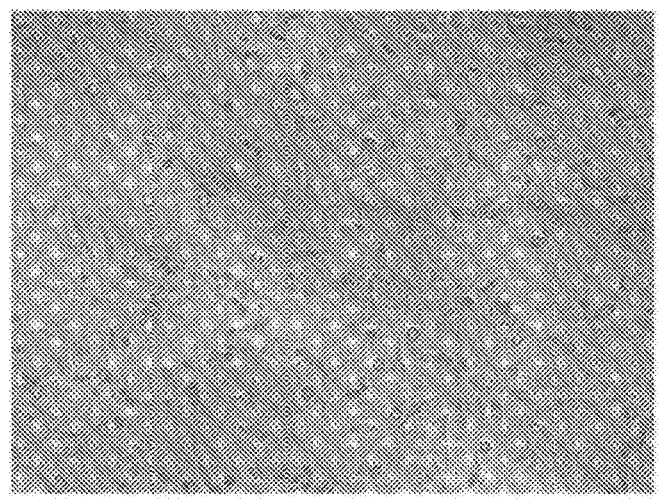
Fig. 12 shows results of a biocompatibility study carried out with mouse fibroblasts L929, which were applied to the smooth surface of cured material.

A form with resin prepared according to 4.2, variant (b) was radiated with UV light. After curing, a biocompatibility study was carried out with mouse fibroblasts L929, which were applied to the smooth surface of the cured material. After three days, the material was colonized with cells. These had spread out ("spreading") in all directions, as can be seen in FIG. 12, which is a sign that they are doing well.

Example 5

Functionalization of Polycaprolactone-Diol with Di(Ethylene Glycol)-Dimethacrylate and Organic Polymerization of the Product

5.1 Preparation of (6-methacroyl)hexanoic acid(di(ethylene glycol)methacrylate)ester 4.72 g (8.90 mmol) of polycaprolactonediol, 20.0 mL (21.64 g, 89.3 mmol) of di(ethylene glycol)-dimethacrylate and 0.50 mL (0.48 g, 1.70 mmol) of tetraisopropyltitanium (IV) were charged under nitrogen atmosphere in a 100-mL Schlenck flask with reflux condenser and the yellow reaction solution was heated at 135° C. After four hours the solution was cooled off in air for 30 min. and 10.0 mL of water were added, whereby a yellowish precipitate immediately precipitated out. The precipitate was centrifuged off for 10 min. at 4,000 rpm after another 15 hr., washed with a small amount of pentane and centrifuged off again. The organic solutions were washed three times with 10 mL of water each. The solvent was removed by distillation, so that a colorless solution remained behind. This colorless liquid was then purified by column chromatography with n-pentane:ethyl acetate=5:1 as the eluent.

Yield: 5.754 g (16.15 mmol, 45.4%)

$^1$H-NMR (CDCl$_3$, 23° C., 400.1 MHz, [ppm]): δ=1.35 (m, 2H, C=OOCH$_2$CH$_2$CH$_2$CH$_2$CH$_2$C=OO), 1.61 (m, 4H, C=OOCH$_2$CH$_2$CH$_2$CH$_2$CH$_2$C=OO), 1.86 (s, 3H, H$_2$C=CCH$_3$C=OOCH$_2$CH$_2$CH$_2$CH$_2$CH$_2$C=O), 1.87 (s, 3H, OCH$_2$CH$_2$OC=OCCH$_3$=CH$_2$), 2.28 (t, $^3J_{HH}$=7.58 Hz, 2H, C=OCCH$_2$CH$_2$CH$_2$CH$_2$C=OO), 3.64 (t, $^3J_{HH}$=4.80 Hz, 2H), 3.67 (t, $^3J_{HH}$=4.92 Hz, 2H, C=OCCH$_2$CH$_2$OCH$_2$CH$_2$OC=O), 4.06 (t, $^3J_{HH}$=6.57 Hz, 2H, C=OCCH$_2$CH$_2$CH$_2$CH$_2$C=OO), 4.16 (t, $^3J_{HH}$=4.67 Hz, 2H, C=OCCH$_2$CH$_2$OCH$_2$CH$_2$OC=O), 4.23 (t, $^3J_{HH}$=4.80 Hz, 2H, C=OCCH$_2$CH$_2$OCH$_2$CH$_2$OC=O), 5.47 (t, $^4J$=1.52 Hz, 1H, H$_2$C=CCH$_3$C=OOCH$_2$CH$_2$CH$_2$CH$_2$=O cis), 5.51 (t, $^4J$=1.52 Hz, 1H, OCH$_2$CH$_2$OC=OCCH$_3$=CH$_2$ cis), 6.01 (s, 1H, H$_2$C=CCH$_3$C=OOCH$_2$CH$_2$CH$_2$CH$_2$=O trans), 6.05 (s, 1H, OCH$_2$CH$_2$OC=OCCH$_3$=CH$_2$ trans).—$^{13}$C-NMR (CDCl$_3$, 23° C. 100.6 MHz, [ppm]): δ=17.31, 17.32 (CH$_3$), 23.51 (C=OOCH$_2$CH$_2$CH$_2$CH$_2$C=OO), 24.56 (C=OOCH$_2$CH$_2$CH$_2$CH$_2$C=OO), 27.31 (C=OOCH$_2$CH$_2$CH$_2$CH$_2$C=OO), 32.98 (C=OOCH$_2$CH$_2$CH$_2$CH$_2$C=OO), 62.34 (C=OOCH$_2$CH$_2$OCH$_2$CH$_2$OC=O), 62.75 (C=OOCH$_2$CH$_2$OCH$_2$CH$_2$OC=O), 63.44 (C=OOCH$_2$CH$_2$CH$_2$CH$_2$C=OO), 68.05, 68.12 (C=OOCH$_2$CH$_2$OCH$_2$CH$_2$OC=O), 124.28, 124.80 (CCH$_3$=CH$_2$), 135.11, 135.41 (CCH$_3$=CH$_2$), 166.27, 166.43 (C=OCCH$_3$=CH$_2$), 172.43 (C=OOCH$_2$CH$_2$CH$_2$CH$_2$C=OO), FT-IR (ATR, 23° C., [cm$^{-1}$]): $\tilde{v}$=2951 (m, $v_{as}$ (C—H)), 2867 (w, $v_s$(C—H)), 1715 (s, v(C=O)), 1637 (m, v(C=C)), 1296 (s, v(C—O—C)), 1160 (ss, v(C—O—C)), 940 (s, δ(C—H)), 814 (m, skel. bend).

μ-Raman (23° C., [cm$^{-1}$]): $\tilde{v}$=868 (m, v(C—H)), 1444 (m, (δ(C—H)), 1639 (m, v(C=C)), 1718 (m, v(C=O)), 2928 (s, $v_{as}$ (C—H)).

5.2 Preparation of a Curable Resin Using (6-Methacroyl)Hexanoic Acid(Di(Ethylene Glycol)Methacrylate)Ester Analogously to Example 1.2, (6-methacroyl)hexanoic acid(di(ethylene glycol)methacrylate)ester was mixed and treated with a hybrid polymer consisting of 3-methacryloxypropyl trimethoxysilane and diphenylsilanediol, whereby the components were used in the molar ratio of 50% methacrylate ester and 50% hybrid polymer.

5.3 Polymerization of the Resin Under UV Radiation

Figure 13:
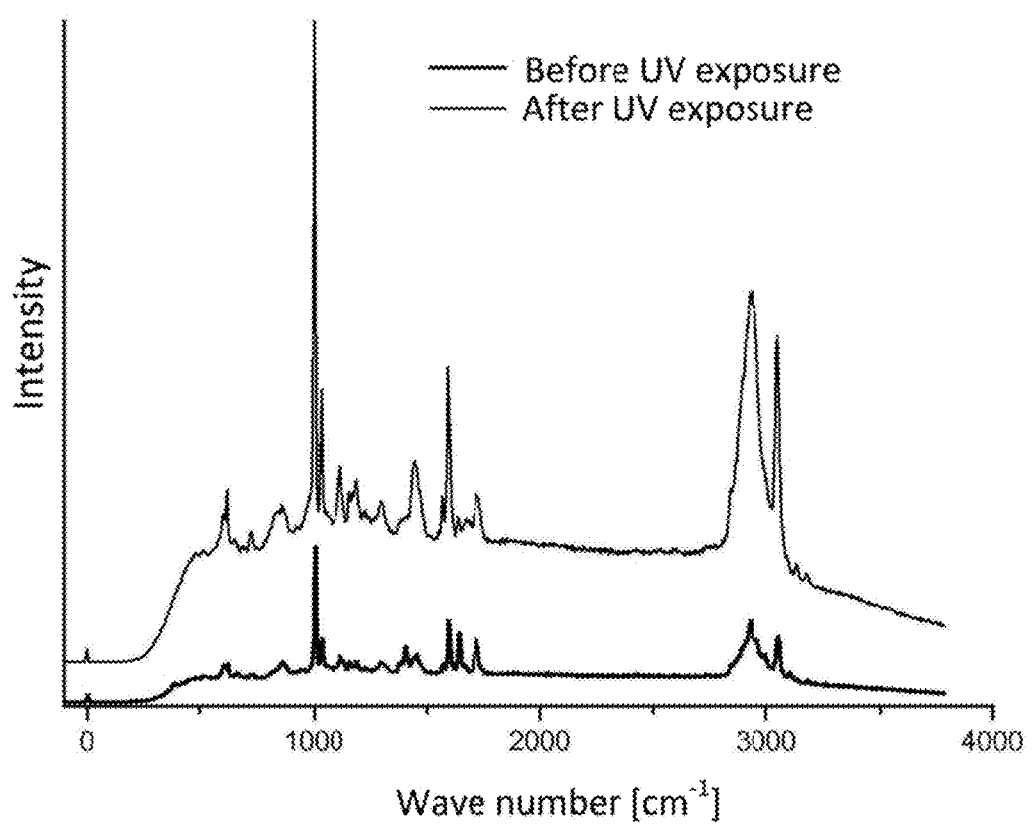
Fig. 13 depicts a μ-Raman spectrum of an alternative resin polymerized using exposure to UV light, before and after polymerization.

The resin prepared according to 5.2 was filled into a form and organically polymerized (cured) by means of exposure to UV light. The μ-Raman spectrum before and after polymerization is shown in FIG. 13. A marked decrease in the C=C band is seen at 1648 cm$^{-1}$ compared to the C=O band at 1722 cm$^{-1}$ as a result of the organic crosslinking.

Example 6

Functionalization of 1,2:5,6-Di-O-Isopropylidene-D-Mannitol with Methacrylic Acid Anhydride 3.01 g (11.5 mmol) of 1,2:5,6-di-O-isopropylidene-D-mannitol, as well as 15.0 mL of pyridine were charged into a 100-mL flask with attached reflux condenser and stirred until complete dissolution of the mannitol. 3.00 mL (3.13 g, 20.3 mmol) of methacrylic acid anhydride were then added and the solution was stirred under reflux for another 3.5 hr. at 65° C. 16.2 mL of water were then added and the colorless solution was further stirred for another hour at 65° C. The mixture was cooled off to 30° C. and stirred for 17 hr. After these 17 hr. the solution was extracted three times with 10.0 mL of pentane each. The organic phases were combined, washed three times with 20 mL of water each and three times with 20 mL of 5% sodium hydrogen carbonate solution each and dried over sodium sulfate. After filtering off the desiccant, a clear, colorless liquid is obtained. The solvent was dissolved off and the product was dried in the oil pump vacuum, whereupon a colorless solid was obtained.

Example 7

Synthesis of O-(Methacryloxyethyl)-N-(Triethoxysilylpropyl)Urethane, Preparation of Formed Pieces with the Use Thereof as Well as Degradation and Biocompatibility Studies Thereon

7.1 Synthesis of O-(methacryloxyethyl)-N-(triethoxysilylpropyl)urethane 247 g (1 mol) of (3-isocyanatopropyl)triethoxysilane were slowly added to a mixture of 130 g (1 mol) of (hydroxyethyl)methacrylate, 150 mg of hydroquinone monomethyl ether and 180 mg of dibutyl tin dilaureate and the solution was stirred for 24 hr. at room temperature. The isocyanate IR band at 2245 cm$^{-1}$ could then no longer be observed. The product has the following structural formula:

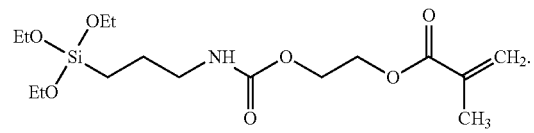 [SMILES: C=C(C)C(=O)OCCOC(=O)NCCC[Si](OCC)(OCC)OCC]

This molecule offers the possibility of organic-photochemical crosslinking at the methacrylate group, can form an inorganic network using the alkoxysilane units and can degrade at the carbamate group.

7.2 Crosslinking of O-(Methacryloxyethyl)-N-(Triethoxysilylpropyl)Urethane by Means of Hydrolytic Condensation of Silyl Groups In a 50-mL round flask, 15.17 g of O-(methacryloxyethyl)-N-(triethoxysilylpropyl)urethane were dissolved in 25 mL of ethyl acetate. 1.8 mL of 0.5 M hydrochloric acid (solution consisting of 192 mL of water and 8 mL of concentrated hydrochloric acid) were then added and the whitish, cloudy solution was stirred for 24 hr. under exclusion of light. It was then washed three times with 23 mL of distilled water each and the pH was checked after each washing step. After drying the mixture by means of hydrophobic filter paper, the solvent was removed by distillation and a viscous, slightly yellowish liquid was obtained.

$^1$H-NMR ([D$_6$]acetone, 23° C., 400.1 MHz, $^{[ppm]}$): δ=0.66 (m, 2H, NHCH$_2$CH$_2$CH$_2$Si), 1.66 (m, 2H, NHCH$_2$CH$_2$CH$_2$Si), 1.91 (s, 3H, H$_2$C=CCH$_3$C(O)O), 3.14 (m, 2H, NHCH$_2$CH$_2$CH$_2$Si), 4.30 (m, 4H, C(O)OCH$_2$CH$_2$OC(O)), 5.62 (m, 1H, O(O)CCCH$_3$=CH$_2$ cis), 6.08 (m, 1H, O(O)CCCH$_3$=CH$_2$ trans).—$^{29}$Si—NMR ([D₆]acetone, 23° C., 79.50 MHz, [ppm]): δ=−66.52-−63.88 (m, T³, NHCH₂CH₂CH₂Si(OSi)₃), −60.64-59.49 (m, T², NHCH₂CH₂CH₂Si(OSi)₂(OEt)), −57.99-1-57.41 (m, T², NHCH₂CH₂CH₂Si(OSi)₂(OH)), −56.11-48.77 (m, T¹, NHCH₂CH₂CH₂Si(OSi)(OEt)₂, 2(NHCH₂CH₂CH₂Si(OSi)(OEt)(OH), NHCH₂CH₂CH₂Si(OSi)(OH)₂).

FT-IR (ATR, 23° C., [cm⁻¹]): ṽ=3338 (m, ν(N—H)), 1698 (s, ν(C=O)), 1636 (m, ν(C=C)), 1530 (s, ν(CHN)), 1450 (m, δ_{as}(C—H)), 1246 (s, ν_{as}(C—O—C)), 1045 (s, ν(Si—O—Si)).

μ-Raman (23° C., [cm⁻¹]): ṽ=539 (m, ν(C=O)), 1295 (m, ν(C—O—C)), 1407 (s, δ(=CH₂)), 1444 (s, δ(CH₂)), 1639 (s, ν(C=C)), 1718 (s, ν(C=O)), 3363 (w, ν(N—H)).

Yield: 12.79 g

7.3 Polymerization of the Condensate by Means of UV Radiation

Figure 14:
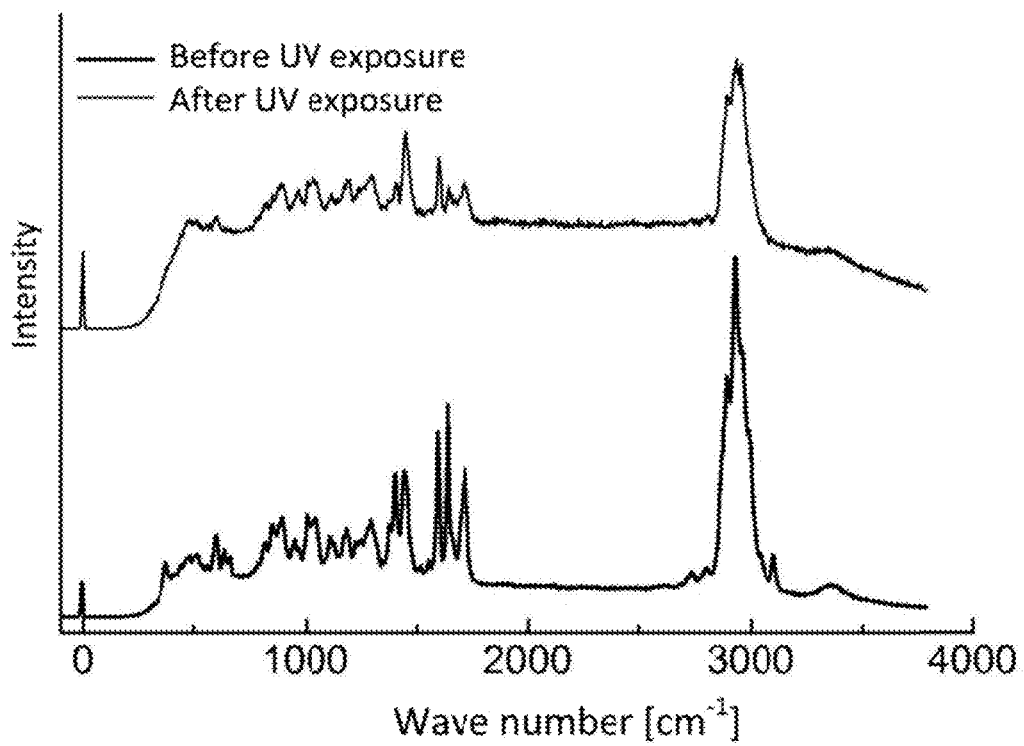
Fig. 14 depicts the IR spectrum of a particular resin polymerized using exposure to UV light, before and after polymerization.

The resin (polycondensate) prepared according to 7.2 was mixed with 2 wt. % of Irgacure® 369, filled into a form and organically polymerized (cured) by means of exposure to UV light. The IR spectrum before and after polymerization is shown in FIG. 14. A marked decrease in the C=C band is seen at 1640 cm⁻¹ compared to the C=O band at 1718 cm⁻¹ as a result of the organic crosslinking.

7.4 Preparation of Formed Pieces by Means of Two-Photon Absorption

Figure 15:
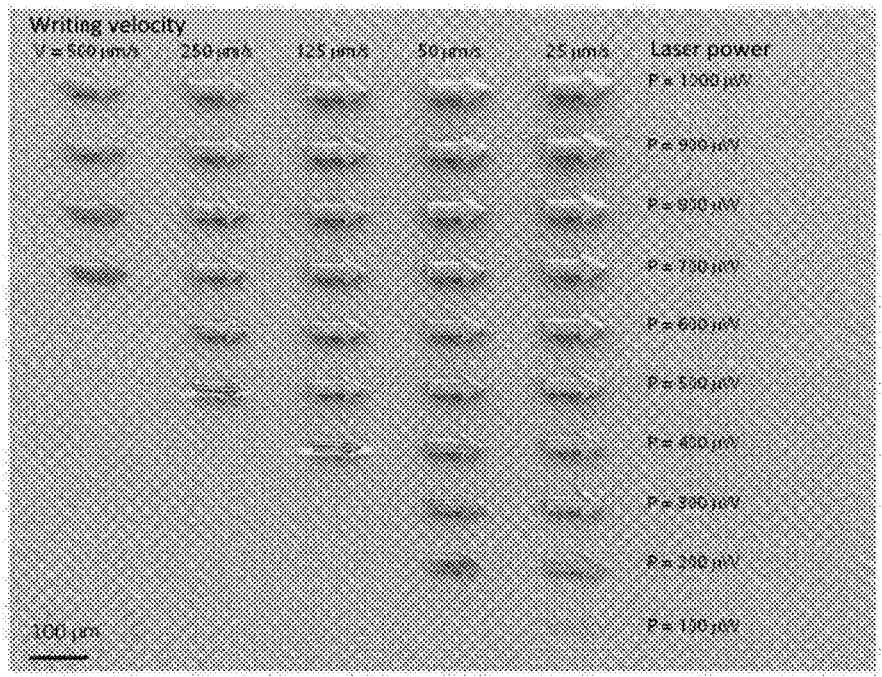
Fig. 15 shows a series of results (using different writing velocities and laser powers) of a particular resin prepared by means of two-photon absorption.
Figure 16:
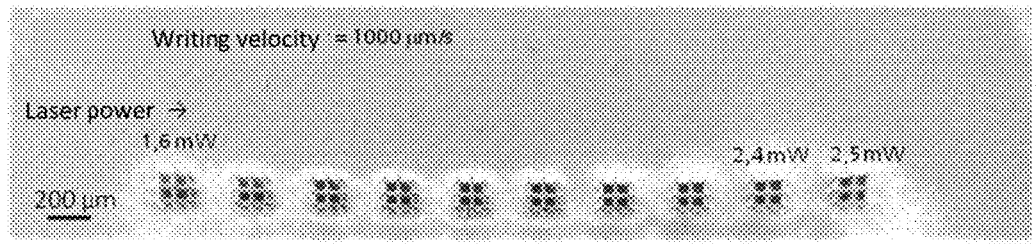
Fig. 16 shows especially fine structurings (formation of channels, preliminary study for the production of scaffolds).

The resin (polycondensate) prepared according to 7.2 was organically polymerized by two-photon absorption (TPA) and structured as indicated above in the "multiphoton polymerization" general example. Different writing velocities and laser powers were used. FIG. 15 shows a series of results in comparison. Especially fine structurings (formation of channels, preliminary study for the production of scaffolds) are shown in FIG. 16. Here, the laser power was increased from 1.6 mW to 2.5 mW with a constant writing velocity of 1,000 μm/sec. layer by layer.

7.5 Scaffold Preparation

Figure 17:
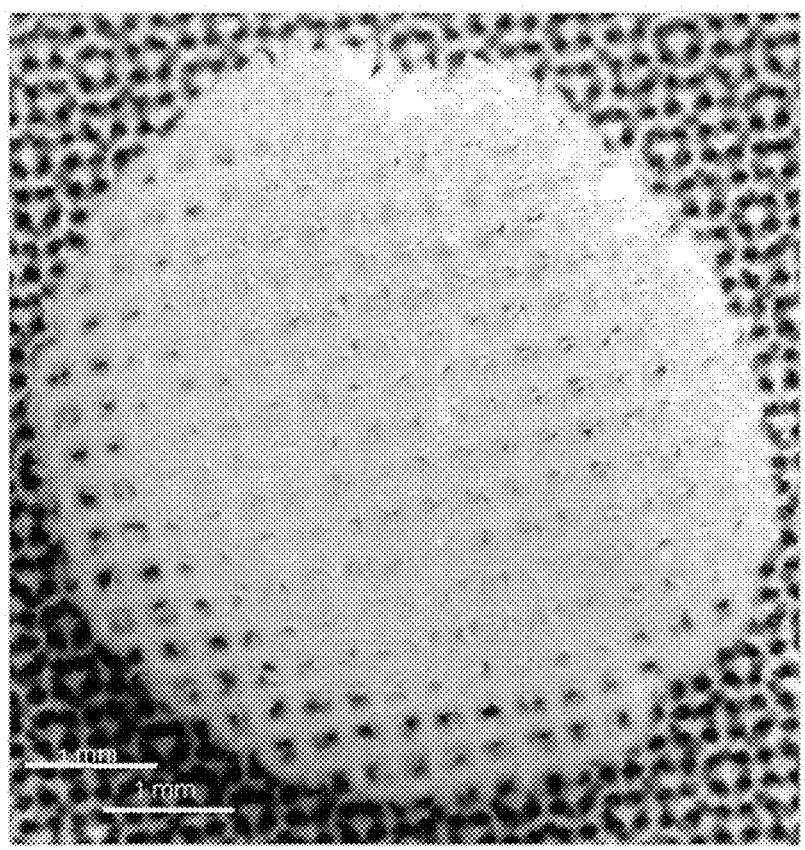
Fig. 17 shows the scaffold of a particular resin prepared by means of two-photon absorption.

The resin (polycondensate) prepared according to 7.2 was organically polymerized by two-photon absorption (TPA) and structured as indicated above in the "multiphoton polymerization" general example under the conditions given below and with the given dimensions. The scaffold is shown in FIG. 17.

Design:
Diameter 5.5 mm, height ca. 1.2 mm
cubic pores (200 μm side length)
Processing
1. Two-photon polymerization with standard exposure setup (see FIG. 1, which is explained in detail in WO 03/037606 A1 as well)
2. Development (3 hr. in isopropyl alcohol/MBIK (1:1))
3. Subsequent exposure to UV light with the mask aligner (20 mW/cm² for 3 min.)

7.6 Degradation Study

Figure 18:
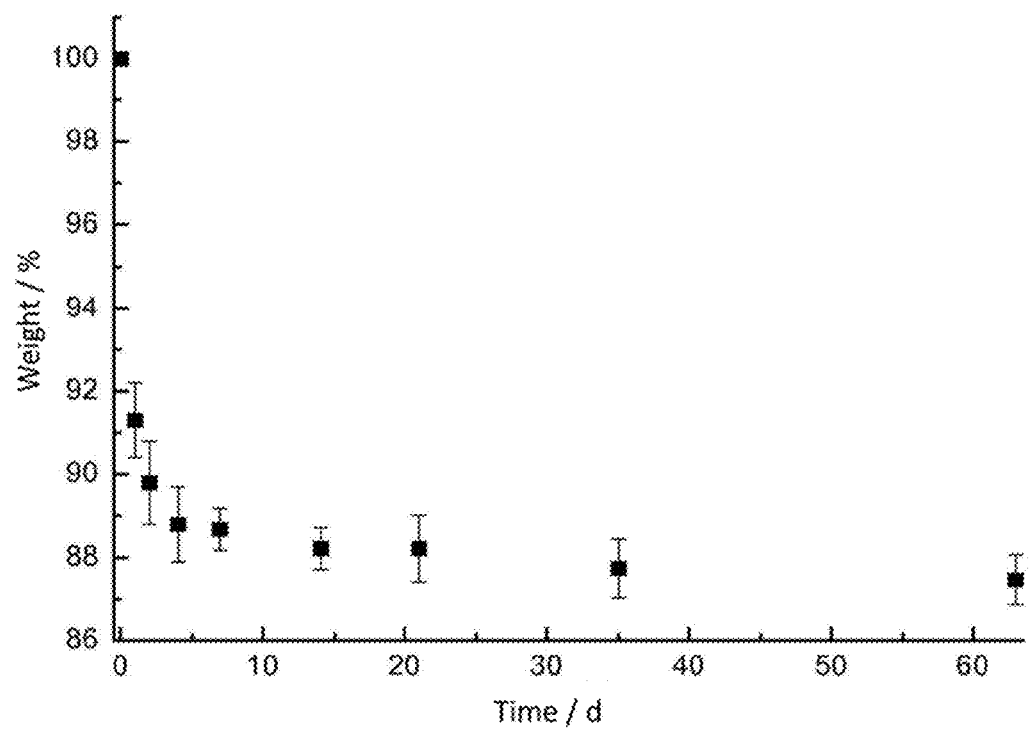
Fig. 18 graphically shows the result of a particular resin prepared in accordance with the present invention and placed in PBS solution.

The resin (polycondensate) prepared according to 7.2 was cured as explained in the general example and then placed in PBS solution. The result is graphically shown in FIG. 18.

7.7 Biocompatibility Study

Figure 19:
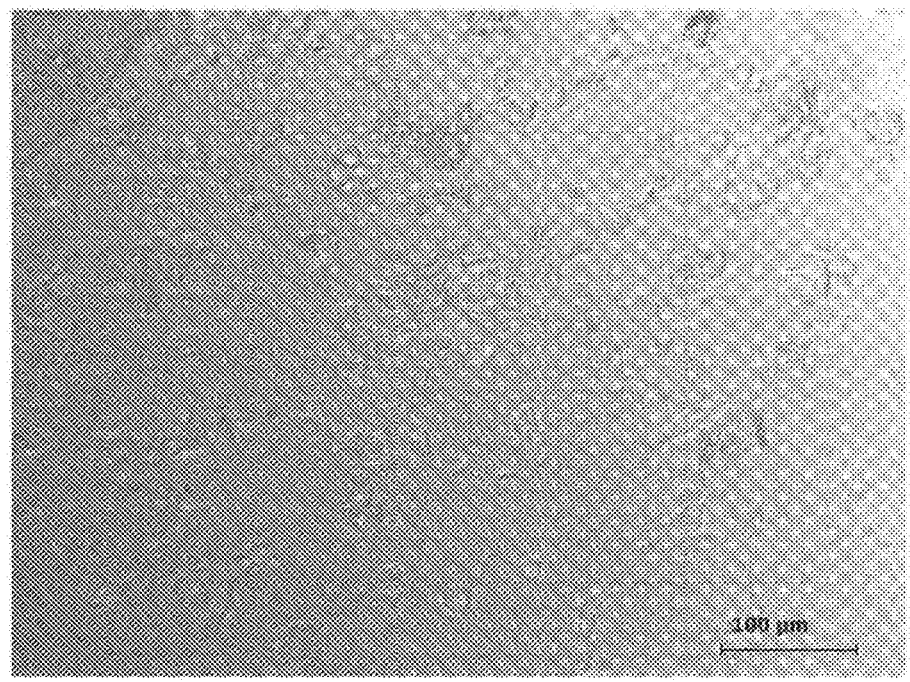
Fig. 19 shows results of an additional biocompatibility study carried out with mouse fibroblasts L929, which were applied to the smooth surface of cured material.

The resin prepared according to 7.2 was radiated with UV light. After the curing, a biocompatibility study was carried out with mouse fibroblasts L929, which were applied to the cured material (bulk material). After 7 days the material was colonized with cells. These had spread out ("spreading") in all directions, as can be seen in FIG. 19, which is a sign that they are doing well.

Therefore, the present invention provides, among other things, the following processes, objects and use possibilities:

1. Process for the production of three-dimensional, self-supporting and/or substrate-supported formed pieces or of structures on surfaces by means of a site-selective solidification of a liquid to pasty, organically modified material within a bath comprising this material by means of two-photon or multiphoton polymerization, whereby the material contains groups or radicals that are available for an inorganic crosslinking or are already inorganically crosslinked, and wherein both an organic radical polymerizable via two-photon or multiphoton polymerization and a biocompatible, biodegradable or bioresorbable radical must be contained in the material, wherein the material comprises an initiator for said two-photon or multiphoton polymerization and one or more components, selected from compounds having an organic radical polymerizable via two-photon or multiphoton polymerization and compounds which carry at least one biocompatible, biodegradable or bioresorbable radical, providing that if at least one purely organic compound which has both an organic radical polymerizable via two-photon or multiphoton polymerization and a biocompatible, biodegradable or bioresorbable radical is present in the material, this compound is selected from among compounds of formula (A)

$$R'—CHR''—O—C(O)—CR'''—CH_2 \qquad (A)$$

wherein the radical R''' is H or CH₃ and wherein R'CHR'' is derived from a compound R'—CHR''OH, selected from among
(a) monosaccharides, selected from the group consisting of aldo- and keto-pentoses, -hexoses and -heptoses with at least one free hydroxyl group, wherein the non-free hydroxyl groups are present in the protected form, dimeric, oligomeric or polymeric carbohydrates, which contain at least one of said monosaccharides,
(b) monomeric or oligomeric or polymeric sugar alcohols, obtainable by means of reduction of the aldehyde or keto group in the molecules mentioned under (a), or
(c) saturated monomeric, oligomeric or polymeric monohydroxy acids as well as their lactones and lactides, selected from among α-hydroxy acids and ω-hydroxy acids.

2. Process in accordance with claim 1, wherein the biocompatible, biodegradable or bioresorbable radical is such a radical that has at least one group, which is selected from among —O—, —OC(O)O—, —C(O)NH—, —NHC(O)NH—, —NHC(O)O—, —C(O)OC(O)— and —C(O)O—, and/or that is split in the human or animal body under physiological conditions or due to the involvement of microorganisms.

3. Process in accordance with claim 1, wherein the bath material contains an organically modified polysiloxane, which is obtainable by means of hydrolysis and at least partial condensation of a starting material, which contains at least one silane of formula (I)

$$R^1_a R^2_b SiX_{4-a-b} \qquad (I)$$

as well as possibly additionally at least one compound of the type $$M^{III}(OR^3)_3 \qquad (II)$$

and/or of the type $$M^{IV}(OR^3)_4 \quad \text{(III)}$$

and/or wherein the bath material has at least one not yet hydrolytically condensed compound (I) and possibly compounds of type (II) and/or (III), wherein M is selected from the group consisting of boron, aluminum and transition metals, $R^1$ is identical or different and represents an organic radical polymerizable via two- or multiphoton polymerization, $R^2$ is identical or different and is an organic radical not polymerizable in this way, $R^3$ represents an alkoxy group, and X is —OH or a radical hydrolytically condensable under conditions of hydrolysis, subscript a is 0, 1, 2 or 3, subscript b is 0, 1 or 2 and a+b together are 0, 1, 2 or 3.

4. Process in accordance with claim 1, wherein the bath material contains an organically modified polysiloxane, which is obtainable by means of hydrolysis and at least partial condensation of at least one silane of formula (Ia)

$$R^1{}_aR^2{}_bSiX_{4-a-b} \quad \text{(Ia)}$$

as well as possibly additionally at least one compound of the type $$M^{III}(OR^3)_3 \quad \text{(II)}$$

and/or of the type $$M^{IV}(OR^3)_4 \quad \text{(III)}$$

and/or at least one not yet hydrolytically condensed compound (Ia) and possibly compounds of type (II) and/or (III), wherein M is selected from the group consisting of boron, aluminum and transition metals, $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is —OH or a radical hydrolytically condensable under conditions of hydrolysis, subscript a is 1, 2 or 3, subscript b is 1 or 2 and a+b together are 2 or 3.

5. Process in accordance with claim 1, wherein the bath material contains an organically modified polysiloxane, which is obtainable by means of hydrolysis and at least partial condensation of a starting material, which contains at least one silane of formula (Ib)

$$R^1{}_aR^2{}_bSiX_{4-a-b} \quad \text{(Ib)}$$

as well as possibly additionally at least one compound of the type $$M^{III}(OR^3)_3 \quad \text{(II)}$$

and/or of the type $$M^{IV}(OR^3)_4 \quad \text{(III)}$$

and/or wherein the bath material contains at least one not yet hydrolytically condensed compound (Ib) and possibly compounds of type (II) and/or (III), wherein M is selected from the group consisting of boron, aluminum and transition metals, $R^1$ is identical or different and represents an organic radical polymerizable via two- or multiphoton polymerization, which additionally has a biocompatible, biodegradable or bioresorbable portion, $R^2$ represents an organic radical not polymerizable via two- or multiphoton polymerization, $R^3$ represents an alkoxy group and X is —OH or a radical hydrolytically condensable under conditions of hydrolysis, subscript a is 1, 2 or 3, subscript b is 0, 1 or 2 and a+b together are 1, 2 or 3.

6. Process in accordance with claim 1, wherein the bath material has at least one purely organic compound with a biocompatible, biodegradable or bioresorbable radical as well as either an organically modified polysiloxane, which is obtainable by means of hydrolysis and at least partial condensation of at least one silane of formula (Ia)

$$R^1{}_aR^2{}_bSiX_{4-a-b} \quad \text{(Ia')}$$

as well as possibly additionally at least one compound of the type $$M^{III}(OR^3)_3 \quad \text{(II)}$$

and/or of the type $$M^{IV}(OR^3)_4 \quad \text{(III)}$$

and/or at least one not yet hydrolytically condensed compound (Ia') and possibly compounds of type (II) and/or (III), wherein M is selected from the group consisting of boron, aluminum and transition metals, $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is —OH or a radical hydrolytically condensable under conditions of hydrolysis, subscript a is 1, 2 or 3, subscript b is 0, 1 or 2, and a+b together are 1, 2 or 3.

7. Process in accordance with claim 1, wherein the organically modified material contains at least one purely organic compound, which has an organic radical polymerizable via two-photon or multiphoton polymerization as well as either an organically modified polysiloxane, which is obtainable by means of hydrolysis and at least partial condensation of at least one silane of formula (Ia)

$$R^1{}_aR^2{}_bSiX_{4-a-b} \quad \text{(Ia'')}$$

as well as possibly additionally at least one compound of the type $$M^{III}(OR^3)_3 \quad \text{(II)}$$

and/or of the type $$M^{IV}(OR^3)_4 \quad \text{(III)}$$

and/or at least one not yet hydrolytically condensed compound (Ia'') and possibly compounds of type (II) and/or (III), wherein M is selected from the group consisting of boron, aluminum and transition metals, $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is —OH or a radical hydrolytically condensable under conditions of hydrolysis, subscript a is 0, 1, 2 or 3, subscript b is 1 or 2, and a+b together are 1, 2 or 3.

8. Process in accordance with claim 1, wherein the organically modified material contains
at least one organically modified polysiloxane, which was obtained or is obtainable by means of hydrolysis and at least partial condensation of at least one silane of formula (Ia')

$$R^1{}_aR^2{}_bSiX_{4-a-b} \quad \text{(Ia')},$$

and
at least partial condensation of at least one silane of formula (Ia'')

$$R^1{}_aR^2{}_bSiX_{4-a-b} \quad \text{(Ia'')},$$

as well as possibly additionally at least one compound of the type $$M^{III}(OR^3)_3 \quad (II)$$

and/or of the type $$M^{IV}(OR^3)_4 \quad (III)$$

and/or at least one not yet hydrolytically condensed compound (Ia') and at least one not yet hydrolytically condensed compound (Ia") and possibly compounds of type (II) and/or (III), wherein M is selected from the group consisting of boron, aluminum and transition metals, $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is —OH or a radical hydrolytically condensable under conditions of hydrolysis, subscript a is 1, 2 or 3, and subscript b is 0, 1 or 2 in formula Ia', subscript a is 0, 1, 2 or 3, and subscript b is 1 or 2 in formula Ia", and a+b together are 1, 2 or 3.

9. Process in accordance with claim 1, wherein the organically modified material comprises at least one purely organic compound, which has both an organic radical polymerizable via two-photon or multiphoton polymerization and a biocompatible, biodegradable or bioresorbable radical and the bath material additionally contains an organopolysiloxane, which is obtainable exclusively or additionally by means of at least partial hydrolytic condensation of at least one silane of formula (I)

$$R^1_a R^2_b SiX_{4-a-b} \quad (I)$$

as well as possibly additionally at least one compound of the type $$M^{III}(OR^3)_3 \quad (II)$$

and/or of the type $$M^{IV}(OR^3)_4 \quad (III)$$

and/or not yet hydrolytically condensed compounds (I) and possibly (II) and/or (III), whereby M is selected from the group consisting of boron, aluminum and transition metals, and
  either $R^1$ is identical or different and represents an organic radical polymerizable via two- or multiphoton polymerization, $R^2$ is identical or different and is an organic radical not polymerizable in this way, $R^3$ represents an alkoxy group, and X is —OH or a radical hydrolytically condensable under conditions of hydrolysis, subscript a is 0, 1, 2 or 3, subscript b is 0, 1 or 2 and a+b together are 0, 1, 2 or 3;
  or $R^1$ is identical or different and represents an organic radical polymerizable via two- or multiphoton polymerization, $R^2$ is a biocompatible, biodegradable or bioresorbable radical or has such a radical, $R^3$ represents an alkoxy group and X is —OH or a radical hydrolytically condensable under conditions of hydrolysis, subscript a is 1, 2 or 3, subscript b is 1 or 2 and a+b together are 2 or 3.

10. Process in accordance with claim 3, wherein $R^1$ in formula (I) is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

11. Process in accordance with claim 1, characterized in that different degrees of crosslinking are obtained within the molding by the radiation being carried out with different intensity gradients.

12. Process in accordance with claim 4, wherein $R^1$ in formula (Ia) is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

13. Process in accordance with claim 6, wherein $R^1$ in formula (Ia') is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

14. Process in accordance with claim 7, wherein $R^1$ in formula (Ia") is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

15. Process in accordance with claim 5, wherein $R^1$ in formula (Ib) is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

16. Process in accordance with claim 8, wherein $R^1$ in formula (Ia') or in formula (Ia") is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

17. Process in accordance with claim 9, wherein $R^1$ in formula (I) is a radical containing a nonaromatic C=C double bond, and/or wherein X is hydrogen, halogen, hydroxy, alkoxy, acyloxy or $NR^3_2$ with $R^3$ equal to hydrogen or alkyl with 1 to 6 carbon atoms.

18. Process according to claim 2, wherein said radical has at least one group, selected from the group consisting of —OC(O)O—, —NHC(O)NH—, and —C(O)OC(O)—, or at least two groups, selected from the group consisting of an oxygen bridge between two carbon atoms, —OC(O)O—, —C(O)NH—, —NHC(O)NH—, —NHC(O)O—, —C(O)OC(O)— and —C(O)O—.

19. Process according to claim 11, wherein different intensity gradients are obtained by lowering the intensity and expanding the focus.

* * * * *

UNITED STATES PATENT AND TRADEMARK OFFICE
CERTIFICATE OF CORRECTION

PATENT NO. : 9,539,763 B2
APPLICATION NO. : 13/577731
DATED : January 10, 2017
INVENTOR(S) : Krauss et al.

It is certified that error appears in the above-identified patent and that said Letters Patent is hereby corrected as shown below:

On the Title Page

Item (12) delete "Houbertz-Krauss" and insert --Krauss et al.--.

Item (75) Inventors, should read:
--(75) Inventors: Ruth Krauss, Wuerzburg (DE); Matthias Beyer, Wuerzburg (DE); Joern Probst, Kuernach (DE); Thomas Stichel, Wuerzburg (DE)--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*